US008721997B2

(12) United States Patent
Hechler et al.

(10) Patent No.: US 8,721,997 B2
(45) Date of Patent: May 13, 2014

(54) REACTOR FOR CONTINUOUS HETEROGENEOUSLY CATALYZED PARTIAL DEHYDROGENATION OF AT LEAST ONE HYDROCARBON TO BE DEHYDROGENATED

(75) Inventors: Claus Hechler, Ludwigshafen (DE); Wilhelm Ruppel, Mannheim (DE); Goetz-Peter Schindler, Ludwigshafen (DE); Catharina Klanner, Mannheim (DE); Hans-Juergen Bassler, Neustadt (DE); Martin Dieterle, Ludwigshafen (DE); Karl-Heinrich Klappert, Birkenheide (DE); Klaus Joachim Mueller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 802 days.

(21) Appl. No.: 12/912,127

(22) Filed: Oct. 26, 2010

(65) Prior Publication Data

US 2011/0038763 A1 Feb. 17, 2011

Related U.S. Application Data

(62) Division of application No. 11/767,782, filed on Jun. 25, 2007, now Pat. No. 7,847,118.

(60) Provisional application No. 60/816,592, filed on Jun. 27, 2006.

(30) Foreign Application Priority Data

Jun. 27, 2006 (DE) .......................... 10 2006 029 790

(51) Int. Cl.
*B01J 8/00* (2006.01)

(52) U.S. Cl.
USPC ........... 422/641; 422/651; 422/655; 422/240; 422/241

(58) Field of Classification Search
USPC .................. 422/641, 632, 651, 655, 240, 241; 148/325, 327, 335; 420/43, 94, 100
See application file for complete search history.

(56) References Cited

U.S. PATENT DOCUMENTS

| 4,224,062 | A | * | 9/1980 | Darnfors ......................... 420/40 |
| 4,444,731 | A | * | 4/1984 | Konoki et al. ................. 422/310 |
| 4,770,315 | A | | 9/1988 | Supik |
| 5,406,014 | A | | 4/1995 | Heyse et al. |
| 5,705,684 | A | | 1/1998 | Hefner et al. |
| 5,723,707 | A | | 3/1998 | Heyse et al. |
| 5,997,826 | A | * | 12/1999 | Lodeng et al. ................. 422/634 |
| 6,241,953 | B1 | | 6/2001 | Krijgsman |
| 6,426,433 | B1 | | 7/2002 | Machhammer et al. |
| 6,676,906 | B1 | * | 1/2004 | Heisel ........................... 422/601 |
| 6,781,017 | B2 | | 8/2004 | Machhmanner et al. |
| 6,890,393 | B2 | * | 5/2005 | Buck ............................. 148/325 |
| 7,238,827 | B2 | | 7/2007 | Hechler et al. |
| 7,291,761 | B2 | | 11/2007 | Machhmanner et al. |
| 7,321,058 | B2 | | 1/2008 | Machhmanner et al. |
| 7,348,443 | B2 | | 3/2008 | Proll et al. |
| 2003/0044334 | A1 | | 3/2003 | Kadowaki et al. |
| 2004/0199001 | A1 | | 10/2004 | Schindler et al. |
| 2005/0118088 | A1 | * | 6/2005 | Olbert et al. ................... 423/416 |
| 2006/0004226 | A1 | | 1/2006 | Machhmanner et al. |
| 2007/0088092 | A1 | | 4/2007 | Klanner et al. |
| 2007/0142689 | A1 | | 6/2007 | Hechler et al. |
| 2007/0276157 | A1 | | 11/2007 | Machhammer et al. |
| 2008/0119673 | A1 | | 5/2008 | Hechler et al. |

FOREIGN PATENT DOCUMENTS

| DE | 3522646 | 1/1987 |
| DE | 694 17 879 | 8/1999 |
| DE | 102 45 585 | 4/2004 |
| DE | 103 16 039 | 10/2004 |
| DE | 10 2004 032 129 | 3/2005 |
| DE | 10 2005 051 401 | 4/2007 |
| DE | 10 2005 061 626 | 6/2007 |
| DE | 10 2006 017 623 | 10/2007 |
| DE | 10 2006 024 901 | 11/2007 |
| EP | 0 683760 | 11/1995 |
| EP | 0 731 077 | 9/1996 |
| EP | 0 799 169 | 10/1997 |
| EP | 0 799 169 | 3/2000 |
| GB | 2 066 696 | 7/1981 |
| WO | 00/10961 | 3/2000 |
| WO | 01/96270 A2 | 12/2001 |
| WO | 01/96270 A3 | 12/2001 |
| WO | 01/96271 A2 | 12/2001 |
| WO | 01/96271 A3 | 12/2001 |
| WO | 03/011804 A2 | 2/2003 |
| WO | 03/011804 A3 | 2/2003 |
| WO | 03/076370 | 9/2003 |

* cited by examiner

*Primary Examiner* — Nina Bhat
(74) *Attorney, Agent, or Firm* — Oblon, Spivak, McClelland, Maier & Neustadt, L.L.P.

(57) ABSTRACT

A process for continuous heterogeneously catalyzed partial dehydrogenation of at least one hydrocarbon to be dehydrogenated in a reactor which is manufactured from a composite material which consists, on its side in contact with the reaction chamber, of a steel B with specific elemental composition which, on its side facing away from the reaction chamber, either directly or via an intermediate layer of copper, or of nickel, or of copper and nickel, is plated onto a steel A with specific elemental composition, and also partial oxidations of the dehydrogenated hydrocarbon and the reactor itself.

20 Claims, No Drawings

REACTOR FOR CONTINUOUS HETEROGENEOUSLY CATALYZED PARTIAL DEHYDROGENATION OF AT LEAST ONE HYDROCARBON TO BE DEHYDROGENATED

The present application is a Divisional application of 11/767,782, now U.S. Pat. No. 7,847,118, having a filing date of Jun. 25, 2007 and claiming priority to U.S. 60/816,592 and DE 102006029790.3, both having a filing date of Jun. 27, 2006.

The present invention relates to a process for continuous heterogeneously catalyzed partial dehydrogenation of at least one hydrocarbon to be dehydrogenated in the gas phase, comprising a procedure in which a reaction chamber which is enclosed by a (material) shell (E) which is in contact with the reaction chamber and has at least one first orifice for feeding at least one starting gas stream into the reaction chamber and at least one second orifice for withdrawing at least one product gas stream from the reaction chamber, at least one starting gas stream comprising at least one hydrocarbon to be dehydrogenated is fed continuously,
in the reaction chamber, the at least one hydrocarbon to be dehydrogenated is conducted through at least one catalyst bed disposed in the reaction chamber and, with generation of a product gas comprising the at least one dehydrogenated hydrocarbon, unconverted hydrocarbon to be dehydrogenated and molecular hydrogen and/or steam, is dehydrogenated partially in an oxidative or nonoxidative manner to at least one dehydrogenated hydrocarbon, and
at least one product gas stream is withdrawn continuously from the reaction chamber.

The present invention also relates to an apparatus for carrying out the process according to the invention, and to processes for partial oxidation of the at least one dehydrogenated hydrocarbon.

The term "dehydrogenated hydrocarbon" used in this application is intended to comprise hydrocarbons whose molecules comprise at least two ("two" are preferred from a performance point of view) hydrogen atoms fewer than the molecules of a hydrocarbon to be dehydrogenated. Otherwise, the term hydrocarbon is intended to comprise substances whose molecules are formed only from the elements carbon and hydrogen.

Hence, dehydrogenated hydrocarbons comprise especially acyclic and cyclic aliphatic hydrocarbons having one or more C,C double bonds in the molecule.

Examples of such aliphatic dehydrogenated hydrocarbons are propene, isobutene, ethylene, 1-butene, 2-butene and butadiene. In other words, the dehydrogenated hydrocarbons include in particular the monounsaturated linear hydrocarbons (n-alkenes) or branched aliphatic hydrocarbons (e.g. isoalkenes), and also the cycloalkenes.

Moreover, the dehydrogenated hydrocarbons are also intended to comprise the alkapolyenes (e.g. dienes and trienes) which comprise more than one carbon-carbon double bond in the molecule. However, dehydrogenated hydrocarbons are also intended to comprise hydrocarbon compounds which are obtainable starting from alkylaromatics such as ethylbenzene or isopropylbenzene by dehydrogenation of the alkyl substituents. These are, for example, compounds such as styrene or α-methylstyrene.

Dehydrogenated hydrocarbons are quite generally valuable starting compounds for the synthesis of, for example, functionalized, free-radically polymerizable compounds (e.g. acrylic acid from propene or methacrylic acid from isobutene and polymerization products thereof). For example, such functionalized compounds can be obtained by partial oxidation of dehydrogenated hydrocarbons. However, dehydrogenated hydrocarbons are also suitable for preparing compounds such as methyl tert-butyl ether (subsequent product of isobutene, which is suitable, for example, as a fuel additive for setting the octane number). Dehydrogenated hydrocarbons may also be used as such for polymerization themselves.

Useful hydrocarbons to be dehydrogenated in this document are especially the acyclic and cyclic alkanes, but also olefins (whose C, C double bond number is to be increased) (as an example, mention should be made of the heterogeneously catalyzed partial dehydrogenation of n-butenes to butadiene).

In other words, the term "hydrocarbons to be dehydrogenated" in this patent application comprises, for example, hydrocarbons of the stoichiometry $C_nH_{2n+2}$ where n>1 to n≤20, and of the stoichiometry $C_nH_{2n}$ where n>1 to n≤20, and of the stoichiometry $C_nH_{2n-2}$ where n>2 to n≤20, and n=an integer, especially $C_2$- to $C_{16}$-alkanes, for example ethane (to ethylene), propane (to propylene), n-butane, isobutane (to isobutene), n-pentane, isopentane, n-hexane, n-heptane, n-octane, n-nonane, n-decane, n-undecane, n-dodecane, n-tridecane, n-tetradecane, n-pentadecane and n-hexadecane.

In particular, however, all statements made in this document apply to $C_2$- to $C_6$-alkanes as hydrocarbons to be dehydrogenated and very particularly to $C_2$ to $C_4$ hydrocarbons. In other words, hydrocarbons to be dehydrogenated in this document are in particular ethane, propane, n-butane and isobutane, but also 1-butene and 2-butene.

The process described at the outset for preparing dehydrogenated hydrocarbons is common knowledge (cf., for example, WO 03/076370, DE-A 10 2004 032 129, EP-A 731 077, WO 01/96271, WO 01/96270, DE-A 103 16 039, WO 03/011804, WO 00/10961, EP-A 799 169, DE-A 102 45 585 and German applications 10 2005 061 626, 10 2006 017 623 and DE 102006024901.1).

In principle, the processes for preparing dehydrogenated hydrocarbons by heterogeneously catalyzed partial dehydrogenation of at least one hydrocarbon to be dehydrogenated are divided into two groups: oxidative and nonoxidative heterogeneously catalyzed partial dehydrogenations. In contrast to the oxidative heterogeneously catalyzed partial dehydrogenation, the nonoxidative heterogeneously catalyzed partial dehydrogenation is effected without the action of oxygen. In other words, the hydrogen to be pulled from the hydrocarbon to be dehydrogenated is pulled out immediately as molecular hydrogen and is also not oxidized at least partly oxidatively to water with oxygen in a subsequent step. The thermal character of a nonoxidative dehydrogenation is thus endothermic in every case. In the oxidative heterogeneously catalyzed partial dehydrogenation, in contrast, the molecular hydrogen to be pulled from the hydrocarbon to be dehydrogenated is pulled out under the action of oxygen. It can be pulled out immediately as water ($H_2O$) (this case is also referred to for short as a heterogeneously catalyzed oxydehydrogenation; its thermal character is exothermic in every case). However, it can also be done initially as molecular hydrogen (i.e. nonoxidatively or conventionally) which can then be oxidized partly or fully with oxygen to water ($H_2O$) in a subsequent step (depending on the extent of subsequent hydrogen combustion, the overall thermal character may be endothermic, exothermic or neutral).

It is common to all aforementioned heterogeneously catalyzed partial dehydrogenations of hydrocarbons to be dehydrogenated that they proceed at comparatively high reaction temperatures. Typical reaction temperatures may be ≥250° C., frequently ≥300° C., often ≥350° C., or ≥400° C., or ≥450° C., or ≥500° C.

In the course of long-term operation of a continuous heterogeneously catalyzed partial dehydrogenation, moreover, even higher reaction temperatures are normally required increasingly with the operating time, in order to maintain the dehydrogenation conversion in single pass through the reaction chamber. This is typically because the catalysts used become irreversibly deactivated to an increasing extent with increasing operating time. In other words, even when the continuous operation is interrupted temporarily time and again (such an operating mode is intended to be comprised by the term "continuously" in this document), in order to reactivate (to regenerate) the catalysts used by means of suitable measures, the original activity of the catalysts with the overall operating time is increasingly no longer attained with increasing overall operating time of the process. Corresponding increase in the reaction temperature can counteract this fact. An increase in the reaction temperature is, though, normally also used to counteract the reversible deactivation of the catalyst.

A disadvantage of such high reaction temperatures is that, relative to the desired target reaction (hydrocarbon to be dehydrogenated→dehydrogenated hydrocarbon), undesired side reactions increasingly gain increasing weight to an extent generally increasing with the reaction temperature. One of these undesired side reactions is, for example, the thermal decomposition of the hydrocarbon to be dehydrogenated and/or of the dehydrogenated hydrocarbon, typically to hydrocarbons having a smaller number of carbon atoms.

The conventional material for the shell of reaction chambers for industrial scale production is steel. However, experimental investigations have found that steel, as a material for the side in contact with the reaction chamber of the shell of a process as described at the outset, is capable of catalyzing the thermal decomposition of hydrocarbons to be dehydrogenated and/or of dehydrogenated hydrocarbons. The catalytic action reduces the activation energy required for the thermal decomposition, which makes this undesired side reaction noticeable in an undesirable manner even at comparatively low reaction temperatures. In a corresponding manner, steel in the presence of molecular oxygen is also capable of catalyzing the combustion of hydrocarbon to be dehydrogenated and/or of dehydrogenated hydrocarbon. What is significant in the aforementioned context is that the extent of the catalytic action depends upon the elemental composition of the particular steel.

Against the above background, the prior art recommends different steels for the process described at the outset. WO 03/076370 recommends, for example, in its working examples, as a material for the shell, steel which has been alonized, alitized and/or aluminized (i.e. coated, respectively, with aluminum, with aluminum oxide or with aluminum and aluminum oxide) on the side of the shell in contact with the reaction chamber. No further statements regarding the composition of the steel are made by WO 03/076370. The same recommendation is made by WO 03/011804. As a possible alternative, it additionally recommends the use of sulfides in the starting gas stream for the purpose of passivating the side of the shell in contact with the reaction chamber.

However, a disadvantage of an alonization or alitization and/or alumination is that it can be performed on the industrial scale only at exceptional cost. A disadvantage of use of sulfides in the starting gas stream is firstly the demand therefor and secondly that such a use generally has an adverse effect on the lifetime of the catalysts used for the heterogeneously catalyzed partial dehydrogenation and/or an adverse effect on the lifetime of the catalysts used for a heterogeneously catalyzed partial oxidation of the dehydrogenated hydrocarbon which follows if appropriate.

The aforementioned disadvantages are not possessed by the teaching of DE A 102004032129 which recommends, as the material for the shell in its comparative example, uncoated steel of DIN materials number 1.4841. This is a steel which may have the following elemental composition:

from 24 to 26% by weight of Cr,
from 19 to 22% by weight of Ni,
from 1.5 to 2.5% by weight of Si,
from ≥0 to 0.11% by weight of N,
from ≥0 to 0.2% by weight of C,
from ≥0 to 2% by weight of Mn,
from ≥0 to 0.045% by weight of P,
from ≥0 to 0.015% by weight of S, and,
apart from these, Fe and impurities resulting from production, the percentages each being based on the total weight.

In a similar manner, DE-A 10 2005 051 401 recommends Si-containing steels, for example those of the DIN 1.4841 type, as a material for the shell. Among other recommendations, DE 102006017623.5 also comprises the recommendation of DIN 1.4841-type steel for the side in contact with the reaction chamber.

As an alternative to DIN materials number 1.4841 steel, DE 102005061626.7 recommends, for the relevant reaction chamber shell, the use of an Si-containing steel which has the following elemental composition:

from 18 to 30% by weight of Cr,
from 9 to 37% by weight of Ni,
from 1 to 3% by weight of Si,
from 0.1 to 0.3% by weight of N,
from ≥0 to 0.15% by weight of C,
from ≥0 to 4% by weight of Mn,
from ≥0 to 4% by weight of Al,
from ≥0 to 0.05% by weight of P,
from ≥0 to 0.05% by weight of S, and,
from ≥0 to 0.1% by weight of one or more rare earth metals, and
apart from these, Fe and impurities resulting from production, the percentages each being based on the total weight, It is assumed in DE 102005061626.7 that the aforementioned steel compositions are selected such that they are also advantageous with regard to the remaining profile of requirements resulting from the relevant production process. This profile of requirements includes, for example, that the steel to be used should also be suitable as a pressure vessel material, since the process described at the outset and accompanying regeneration cycles are preferably performed at working pressures above 1 atm (for example at least 0.5 bar above atmospheric pressure). For example, the German pressure vessel regulations in this respect require a material qualified as suitable to have a notched impact resistance (notched impact energy) (based on room temperature (approx. 25° C.) and standard pressure (1 atm)) of ≥40 J (determined in the notched bar impact test to DIN 50115 in conjunction with DIN EN 10045 part 1 and 2 (in the case of ultrasmall samples); in the test, a pendulum hammer falls from a specified height and hits the back of a notched sample at its lowest point; when the sample is penetrated, some of the hammer energy is consumed for the so-called notched impact energy; this can either be measured on the drag indicator of the instrument or, in the case of instrumented pendulums, further processed directly by electronic means). The direct consequence of the above is the requirement for a low long-term embrittlement tendency of the steel under the process conditions to be employed for the process described at the outset, since the embrittlement of a material is accompanied by decreasing notched impact resistance thereof.

These process conditions include in particular the elevated reaction and/or catalyst regeneration temperatures normally to be employed in the processes mentioned.

Furthermore, the carburization tendency of the steel mentioned should be at a minimum under the conditions of the relevant process. Carburization is the attack on the material of the side in contact with the reaction chamber by elemental carbon which is formed by hydrocarbon decomposition and diffuses into the steel. In contrast to the above-described long-term embrittlement, which covers the entire steel structure from the start onward, the carburization works starting from the surface of the side in contact with the reaction chamber only gradually into the material interior.

The material properties worsen with increasing carburization (for example, the brittleness is increased in regions with carburization; owing to carbide formation of relevant elements, the undesired catalytic effects frequently intensify). In a particularly simple manner, carburization can be investigated metallographically in the case of use of tubular reaction chambers. To this end, a cross section is taken from the particular tubular reactor transverse to its longitudinal axis after the particular operating time. This is ground and polished and then treated first with 65% by weight (65 g of $HNO_3$ in 35 g of $H_2O$) aqueous nitric acid and then after treated with 10% by weight ethanolic acetic acid (10 g of acetic acid in 90 g of ethanol), so that the steel structure becomes visible under the microscope. A structure which has been changed by incorporation of carbon appears dark-grey to black. The carburization depth can be determined starting from the surface with a scale. Frequently, the appearance of carburization is accompanied by a special case of corrosion, known as "metal dusting". This metal attack is pronounced local corrosion which is generally accompanied by formation of depressions. In contrast to carburization, which penetrates comparatively uniformly into the material, metal dusting is characterized by a relatively irregular attack which nonetheless locally progresses comparatively rapidly deep into the material, in which metal carbides formed beforehand decompose with release of carbon and metal particles. At the appropriate surface sites, this attack is clear to the naked eye and visible in a relatively large volume under the microscope in the above-described metallographic examination ("cauliflower formation"). Metal dusting can lead to rapid material failure.

The formation of metal dust is also disadvantageous in that it is distributed, for example, through the reaction gas stream in the entire reaction chamber, including the catalyst bed. However, the metal dust particles are generally catalytically active particles which promote the formation of elemental carbon from hydrocarbon to be dehydrogenated and/or dehydrogenated hydrocarbon. This is disadvantageous especially when the metal dust particles collect in the catalyst bed and the carbon particles formed there cover the active surface of the catalyst, hence deactivating it prematurely.

Moreover, the steel selected as the material should have scaling resistance under the conditions of the relevant process (scaling=oxidative attack by molecular oxygen present in the reaction atmosphere). The requirement for corrosion resistance is of significance especially considering that the dehydrogenated hydrocarbon formed in the process described in the introduction to this document can be partially oxidized under heterogeneous catalysis in a process which follows such a process (particularly advantageously accompanied by the unhydrogenated hydrocarbon). When the desired partial oxidation product is then separated from the product gas mixture of the partial oxidation, what normally remains is a residual gas comprising as yet unhydrogenated hydrocarbon and oxygenates, which is advantageously recycled into the process described in the introduction to this document for the purpose of further conversion of the as yet unhydrogenated hydrocarbon. However, corrosive action can be attributed to the vast majority of all oxygenates (e.g. acrolein, acrylic acid, methacrolein, methacrylic acid, $H_2O$, $O_2$, $CO_2$, etc.).

A further requirement on the steel material selected is that it has to be processable in an advantageous manner. This means in particular that it has to be processable by welding technology, which is not possible in the case of steels alonized prior to the processing without impairing the alonization. However, an alonization after the processing on the industrial scale can be performed only with very great difficulty, if at all.

In-house investigations have now found that none of the steels recommended in the prior art is capable of satisfying the profile of requirements described alone.

Instead, it has been found that generally those steels which have been recommended in the prior art and comprise ≥1% by weight of Si, with regard to their long-term embrittlement tendency, are unsatisfactory under the relevant process conditions.

Conversely, those steels which have been included in the considerations as optional materials in the prior art and have an Si content of ≤0.8% by weight, under the relevant process conditions (especially the elevated reaction and/or catalyst regeneration temperatures), have generally been found essentially not to have long-term embrittlement but exhibit high carburization and metal dusting.

GB-A 2066696 recommends, as a solution to the problem, manufacturing the shell from a nickel-comprising material and coating it with a nickel-free material on its side in contact with the reaction chamber, since especially nickel present in steel is said to promote both carburization and metal dusting (metal dust formation).

EP-A 683 760 subscribes to the teaching of GB-A 2066696 and recommends providing the steel to be used as the material for the shell, on the side in contact with the reaction chamber, with a protective layer which, in particular, according to the granted version of EP-A 683 760 (cf. DE-69417879 T2, granted claims and page 5 lines 20ff. and page 6 lines 25ff.), must necessarily be anchored to the steel via a carbide-rich low-nickel composite intermediate layer. Customary plating is said to be insufficient. Finally, it is also stated that the protective layer must remain intact even in the course of process operation.

Against this background, it was an object of the present invention to provide a material for the shell of reaction chambers for performing a process as described at the outset of this document, which satisfies the profile of requirements described better than the materials disclosed or rendered obvious in the prior art, also including the oxidation/reduction cycles generally to be employed for catalyst regeneration.

The solution provided is a process for continuous heterogeneously catalyzed partial dehydrogenation of at least one hydrocarbon to be dehydrogenated in the gas phase, comprising a procedure in which a reaction chamber which is enclosed by a shell (E) which is in contact with the reaction chamber and has at least one first orifice for feeding at least one starting gas stream into the reaction chamber and at least one second orifice for withdrawing at least one product gas stream from the reaction chamber, at least one starting gas stream comprising at least one hydrocarbon to be dehydrogenated is fed continuously, in the reaction chamber, the at least one hydrocarbon to be dehydrogenated is conducted through at least one catalyst bed disposed in the reaction chamber and, with generation of a product gas comprising the at least one dehydrogenated hydrocarbon, unconverted hydrocarbon to be dehydrogenated and molecular hydrogen and/or steam, is dehydrogenated partially in an oxidative or nonoxidative manner to at least one dehydrogenated hydrocarbon, and at least one product gas stream is withdrawn continuously from the reaction chamber, wherein the shell (E) is manufactured from a composite material which, on its side B in contact with the reaction chamber, consists of steel B of the following elemental composition:

from 18 to 30% by weight of Cr,
from 9 to 37% by weight of Ni,
from 1 to 4% by weight
(or from 1 to 3% by weight) of Si,
from ≥0 to 4% by weight of Al,
from ≥0 to 0.3% by weight of N,
from ≥0 to 0.15% by weight of C,
from ≥0 to 4% by weight of Mn,
from ≥0 to 0.05% by weight of P,
from ≥0 to 0.05% by weight of S, and,
from ≥0 to 0.1% by weight of one or more rare earth metals, and
apart from these, Fe and impurities resulting from production, the percentages each being based on the total weight, with the proviso that the steel B, on its side A facing away from the reaction chamber, is plated either directly or via an intermediate layer of copper, or of nickel, or of copper and nickel, onto steel A of the elemental composition from 15 to 20% by weight of Cr,
from 6 to 18 (preferably from
8 to 16 or to 14) % by weight of Ni,
from ≥0 to 0.8% by weight of Si,
from ≥0 to 0.8% by weight of Al,
from ≥0 to 0.3% by weight of N,
from ≥0 to 0.15% by weight of C,
from ≥0 to 4% by weight of Mo,
from ≥0 to 2.0% by weight of Mn,
from ≥0 to 0.8% by weight of Ti,
from ÷0 to 1.2% by weight,
or to 0.5% by weight of Nb,
from ≥0 to 0.9% by weight of V,
from ≥0 to 0.1% by weight of B,
from ≥0 to 0.05% by weight of P,
from ≥0 to 0.05% by weight of S, and,
apart from these, Fe and impurities resulting from production, the percentages each being based on the total weight, or of the elemental composition from 19 to 23% by weight of Cr,
from 30 to 35% by weight of Ni,
from ≥0 to 1% by weight of Co,
from ≥0 to 1% by weight of Si,
from 0.15 to 0.7% by weight of Al,
from ≥0 to 0.12% by weight of C,
from ≥0 to 2.0% by weight of Mn,
from ≥0 to 0.75% by weight of Cu,
from 0.15 to 0.7% by weight of Ti,
from 0 to 0.05% by weight,
preferably to 0.015% by weight, of P,
from ≥0 to 0.05% by weight,
preferably to 0.01% by weight, of S, and,
apart from these, Fe and impurities resulting from production, the percentages each being based on the total weight, For example, useful steel A for the process according to the invention is that of DIN type 1.4876 (also known as Alloy 800H).

In view of the teachings given in the prior art, it is surprising that the process according to the invention is capable of solving the problem stated in a satisfactory manner, given that steel B in the process according to the invention must comprise at least 9% by weight of Ni.

In agreement with Ullmanns Encyklopädie der technischen Chemie, 4th edition, 1973, volume 3, Verfahrenstechnik und Reaktionsapparate [Process technology and reaction apparatus], Verlag Chemie, Weinheim, page 26ff., plating shall be understood in this document to mean the production of a composite between two or more metal layers, the base material and the applied material, which cannot be separated in hot and cold processing, in welding and in normal stress. Advantageously in accordance with the invention, the composite is such that it meets the requirements of EN 13445-2: 2002 (D) edition 1 (2002-05) for plated products. This applies especially to the industrial supply conditions for plated products for pressure systems according to appendix C.

In other words, as already stated, the bond between base material and applied material must be sufficiently strong that there are no layer separations either in the course of production of the shell (E) nor in the course of operation of the process according to the invention.

Appropriately from an application point of view, the shear resistance of the plating (determined to DIN 50162, September 1978), with a tensile strength of the applied material of less than 280 N/mm$^2$ (determined to DIN 50111), will be more than half of the minimum tensile strength of the applied material and must not be below 140 N/mm$^2$ for all other applied materials irrespective of the testing direction.

Moreover, in inventive composite material, the binding area should advantageously comprise at least 95% of the total contact area, and individual areas surrounded by bonding should not be more than 50 cm$^2$. Plating can be brought about by co-rolling the metals to be bonded (roll plating; K. Born: "Plattierte Bleche für höchste Beanspruchungen" [Plated metal sheets for ultrahigh stresses] in: Werkstofftechnik [Materials technology], DECHEMA Monograph vol. 45, Verlag Chemie, Weinheim 1962), by application welding of the application material to the base material (weld plating; K. Born, W. Speth: Herstellung plattierter Bauteile. Vergleichende Betrachtung zwischen Walzplattieren und Beschichten durch Auftragschweißen [Production of plated components. Comparative evaluation between roller plating and coating by application welding], Schweißen Schneiden, 19, 209-214, 1967) or in such a way that the layers are bonded to one another by a shock-like pressure wave when an explosive explodes (explosive plating; H. C. A. Burkhardt: Schockwellenphysik [Shockwave physics], Metall 19, 1-9, 1965; U. Richter, J. F. Roth: Grundlagen und Anwendung des Sprengplattierens [Fundamentals and use of explosive plating], Naturwissenschaften 57, 487-493, 1970; G. Buck, E. Hornbogen: Metallkundliche Untersuchungen an Explosivschweißnähten [Metallurgy examinations of explosive weld seams], Metall 20, 9-21, 1966).

When the composite material to be used in accordance with the invention has an intermediate layer of copper, or of nickel or of copper and nickel, both steel A and steel B are bonded to this intermediate layer by plating. In the context of, for example, explosive plating, the entire composite may also be obtained in a single working step. Otherwise, the invention does not distinguish whether steel A has been plated onto steel B or vice versa (preferred in accordance with the invention). Instead, the wording "that the steel B, on its side A facing away from the reaction chamber, is plated either directly, or via an intermediate layer of copper, or of nickel, or of copper and nickel, onto steel A" represents both variants. In general, the thinner of the two steels A, B will be plated onto the thicker of the two steels A, B. Further information on the plating of materials can be found by the person skilled in the art in K. Bungardt, G. Lennartz, R. Oppenheim: Einfluss von Stickstoff auf die Eigenschaften austenitischer Chrom-Nickel-und Chrom-Nickel-Molybdän-(Kupfer)-Stähle [Influence of nitrogen on the properties of austenitic chromium-nickel and chromium-nickel-molybdenum-(copper) steels], DEW (Deut. Edelstahlwerke)—Tech. Ber. 7, 71-90, 1967; R. Oppenheim: Chemisch beständige Stähle und Legierungen. Derzeitiger Stand und neuere Entwicklungen [Chemically stable steels and alloys. Current state and recent developments], DEW (Deut. Edelstahlwerke)—Tech. Ber. 7, 49-64, 1967; H. Warwesik: Reaktordruckgefäß [Pressure reactor vessel], Atomwirt., Atomtech. 10, 376-379, 1965; W. Baberg: Dampferzeuger [Steam generator], Atomwirt., Atomtech. 10, 379-381, 1965; W. Klein: Gefügeänderungen beim Explosivplattieren von Stahl mit Stahl und einigen Nichteisenmetallen [Structure changes in the explosive plating of steel with steel and some nonferrous metals], Z. Metallk. 56, 261-267, 1965 and O. Wilms: Anwendung des Sprengplattierens mit Sonderwerkstoffen als Auflage [Use of explosive plating with special materials as the applied layer], DEW (Deut. Edelstahlwerke)—Tech. Ber. 10, 176-183, 1970.

In the plating, the two materials are bonded partly by a mechanical route, partly by a metallurgic route. Overall, a form-fitting bond of the two materials is achieved in the plating.

Advantageously, the composite material to be used in accordance with the invention is obtained by explosive plating. In this case (and generally), steel A preferably forms the base material and steel B the applied material.

It is advantageous in accordance with the invention that steels A and steels B, in the temperature range from 20 to 700° C., have similar coefficients of thermal expansion $\gamma$ (also known as coefficient of longitudinal thermal expansion; it is typically determined on a rod of length 1 m and of homogeneous cross section 1 $cm^2$). The temperature dependencies of the coefficients of thermal expansion $\gamma$ for steels A and steels B are also comparable within the aforementioned temperature range.

Preferably in accordance with the invention, the coefficients of thermal expansion $\gamma$ of steel A present in the inventive composite material and steel B present in the inventive composite material differ by $\leq 2 \cdot 10^{-6}$ m/m·K at 500° C. and 1 atm.

Particularly advantageously, the aforementioned difference is $\leq 1.75 \cdot 10^{-6}$ m/m·K, better $\leq 1.5 \cdot 10^{-6}$ m/m·K, preferably $\leq 1.25 \cdot 10^{-6}$ m/m·K, more preferably $\leq 1.0 \cdot 10^{-6}$ m/m·K, very particularly advantageously $\leq 0.80 \cdot 10^{-6}$ m/m·K, even better $\leq 0.60 \cdot 10^{-6}$ m/m·K or $\leq 0.50 \cdot 10^{-6}$ m/m·K or $\leq 0.40 \cdot 10^{-6}$ m/m·K and at best $\leq 0.30 \cdot 10^{-6}$ m/m·K or $\leq 0.20 \cdot 10^{-6}$ m/m·K, or $\leq 0.10 \cdot 10^{-6}$ m/m·K and at absolute best $\leq 0.05 \cdot 10^{-6}$ m/m·K or 0 m/m·K.

The similarity of the coefficients of thermal expansion $\gamma$ for steels A and B of the composite material to be used in accordance with the invention is of significance because a broad temperature range has to be passed through cyclically as the process according to the invention is practiced, especially owing to the catalyst regeneration to be performed intermediately. Were steels A and B of the composite material to be used in accordance with the invention to have significantly different coefficients of thermal expansion $\gamma$ within this temperature range, the shell which encloses the reaction tube would be deformed like a bimetallic thermometer in the event of the aforementioned temperature variation, which is undesired in a performance of the process according to the invention (this is true especially when steel B becomes brittle in the course of performing the process; corresponding deformations might promote crack and/or fracture formation in steel b). For example, unalloyed or low-alloyed steels (they contain a total amount of <5% by weight of elements other than Fe) or heat resistant martensitic steels having up to 13% by weight of Cr (both of which are typically preferred reactor materials owing to their favorable price) would be unsuitable as plating partners of a steel B for the production of a composite material to be used in accordance with the invention owing to this significantly different $\gamma$ value.

In this document, the expression "copper and/or nickel" shall, in addition to the corresponding pure metals, also comprise alloys which, based on their total weight, comprise up to 5% by weight, or up to 4% by weight, or up to 3% by weight, or up to 2% by weight, or up to 1% by weight, or up to 0.5% by weight of elements (metals) other than copper and/or nickel. They all form comparatively soft intermediate layers (which do not become brittle either), which is why a difference in their thermal coefficient of expansion from that of steels A, B essentially does not have the negative effect described above (they effectively act like a rubber band). In any case, the coefficient of thermal expansion of, for example, pure copper is only insignificantly different from that of steels A, B within the relevant temperature range.

Appropriately from an application point of view, the thickness of steels B in composite materials to be used in accordance with the invention is generally from 0.2 to 25 mm, frequently from 1 to 15 mm or from 1 to 10 mm. Advantageously, the aforementioned thickness is from 2 to 8 mm, preferably from 4 to 6 mm or 5 mm.

The thickness of steels A in composite materials to be used in accordance with the invention is, appropriately from an application point of view, from 10 to 150 mm, in many cases from 20 to 100 mm or from 60 to 100 mm or from 20 (30) to 75 mm or 20 (30) to 50 mm. Typically, the composite material to be used in accordance with the invention comprises steel A and steel B, and also, if appropriate, the intermediate layer, in each case in very constant (uniform) thickness viewed over the composite material.

In the case of a steel A, the material thickness to be selected depends both on the specific steel type and on the diameter of the shell of the reaction chamber. Relatively high thicknesses of the particular steel A are advisable for relatively high diameters, and relatively low thicknesses of the particular steel A for relatively low diameters.

When a DIN type 1.4910 steel A is used, the aforementioned thickness is, preferably in accordance with the invention, from 20 (30) to 50 mm. When a DIN type 1.4941 or DIN type 1.4948 or DIN type 1.4541 steel A is used, the aforementioned thickness is, preferably in accordance with the invention, from 40 or 60 to 100 mm. The lower the stability value (limit of expansion or long-term stability; cf. DIN EN 10028-7) of steel A relevant to the application, the greater the thickness of steel A that will be selected for the composite material to be used in accordance with the invention.

Preferably in accordance with the invention, both the steels A and the steels B are austenitic (stainless) steels. They differ from the ferritic steels (cubic body-centered lattice cells of the crystals) essentially by the different type of lattice structure. In particular, their crystals consist of the more tightly packed cubic face-centered lattice cells. In the production of austenitic steels, the final heat treatment performed is normally solution annealing at temperatures between 1000° C. and 1150° C. with subsequent cooling in water or air in order to prevent the formation of deposits.

When the composite material to be used in accordance with the invention has an intermediate layer of copper, or of nickel, or of copper and nickel, its thickness is normally ≥0.1 mm, usually ≥0.2 mm or ≥0.3 mm. In general, the thickness of this intermediate layer will, however, not exceed 3 mm. In other words, the thickness of the intermediate layer is typically ≤3 mm, or≤2.5 mm, in many cases ≤2 mm, or ≤1.5 mm and preferably ≤1 mm. When an aforementioned intermediate layer is used, no subsequent (on completion of plating) solution annealing should be undertaken.

Subsequent (on completion of plating) solution annealing can be effected (undertaken) without an intermediate layer.

The intermediate layer is capable firstly of contributing to an improvement in the attachment of steel B to steel A, and also of absorbing shear forces which occur in the case of relative motions. Should cracks occur in the steel B over a prolonged operating time in the performance of the process according to the invention, the intermediate layer protects steel A from contact with the reaction gas and thus additionally protects steel A from the risk of carburization and metal dusting. A further advantageous property of the intermediate layer is that it does not become brittle even in the case of contact with the reaction gas.

Advantageously in accordance with the invention, the total amount of the impurities resulting from the production in steels A, B, in quite general terms and on the same basis, is ≤1% by weight, preferably ≤0.75% by weight, more preferably ≤0.5% by weight and most preferably ≤0.25% by weight. In general, the total amount of the impurities of the particular steel A, B resulting from the production will, however, be ≥0.1% by weight. In contrast to the impurities resulting from production, the other constituents of the steel are alloy constituents which determine its properties. This applies in particular to the elements Cr, Ni, Si, N and C, and also Al, Mo, Mn, Ti, V and Nb.

In this document, the rare earth metals comprise the elements cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu). The rare earth metal preferred in accordance with the invention is Ce. Preferably in accordance with the invention, an inventive steel B therefore comprises from ≥0 to 0.1% by weight of Ce, or of Ce and of one or more rare earth metals other than Ce (in particular La, Nd and/or Pr).

A steel B particularly preferred in accordance with the invention is steel of DIN materials number 1.4841.

A steel A particularly preferred in accordance with the invention is steel of DIN materials number 1.4910, which is commercially available, for example, as Thermon® 4910. This steel A is notable for a particularly high high-temperature stability (limit of expansion, long-term stability) with simultaneously high structural stability (high notched impact resistance), especially after long-term use in accordance with the invention, which enables use in comparatively low thicknesses. This is steel within the following composition framework:
 from 16 to 18% by weight of Cr,
 from 12 to 14% by weight of Ni,
 from ≥0 to 0.8% by weight of Si,
 from ≥0.10 to 0.18% by weight of N,
 from ≥0 to 0.1% by weight of C, (preferably from ≥0 to 0.05% by weight)
 from ≥2 to 3% by weight of Mo,
 from ≥0 to 2% by weight of Mn,
 from 0.0015 to 0.0050% by weight of B,
 from ≥0 to 0.05% by weight of P,
 from ≥0 to 0.05% by weight of S, and,
 apart from these, Fe and impurities resulting from production, the percentages each being based on the total weight Advantageously, the P and S contents in the aforementioned composition framework are at the following values:
 from ≥0 to 0.035% by weight of P and
 from ≥0 to 0.015% by weight of S.

Processes according to the invention are very particularly advantageous when the shell of the reaction chamber is manufactured from a composite material whose steel B is a steel of DIN materials number 1.4841 and whose steel A is a steel of DIN materials number 1.4910, steel B being plated (preferably explosively plated) onto steel A either directly or via an intermediate layer of copper, or of nickel, or of copper and nickel.

Advantageously, the thickness of the DIN 1.4910 steel is selected to be from 20 or 30 to 50 mm, and the thickness of the DIN 1.4841 steel to be from 1 to 10 mm, preferably from 4 to 6 mm. When an intermediate layer of Cu, or of Ni, or of Cu and Ni is additionally used, its layer thickness is advantageously from 0.2 to 2 mm, preferably from 0.2 to 1 mm.

Another steel B favorable for the process according to the invention is steel of DIN materials number 1.4828, which may have the following composition:
 from 19 to 21% by weight of Cr,
 from 11 to 13% by weight of Ni,
 from 1.5 to 2.5% by weight of Si,
 from ≥0 to 0.2% by weight of C,
 from ≥0 to 2% by weight of Mn,
 from ≥0 to 0.05% by weight of P,
 from ≥0 to 0.05% by weight of S, and,
 apart from these, Fe and impurities resulting from production, the percentages each being based on the total weight.

Advantageously, the P and S contents in the aforementioned composition framework are at the following values:
 from ≥0 to 0.035% by weight of P and
 from ≥0 to 0.015% by weight of S.

The aforementioned steel is obtainable, for example, from Outokumpu GmbH (D-47877 Willich).

In other words, steels B particularly suitable in accordance with the invention are those whose compositions are within the following composition framework:
 from 19 to 26% by weight of Cr,
 from 11 to 22% by weight of Ni,
 from 1.5 to 2.5% by weight of Si,
 from ≥0 to ≤0.15% by weight of N,
 from ≥0 to ≤5 0.5% by weight of C,
 from ≥0 to ≤5 2% by weight of Mn,
 from ≥0 to 0.05% by weight of P,
 from ≥0 to 0.05% by weight (or from ≥0 to 0.02% by weight) of S, and,
 from ≥0 to 0.1% by weight of one or more rare earth metals, and
 apart from these, Fe and impurities resulting from production, the percentages each being based on the total weight.

In the aforementioned composition frameworks, the P content may also be from ≥0 to ≤0.035% by weight.

Another group S of steels B suitable in accordance with the invention is encompassed under the composition framework
from 18 to 30% by weight of Cr,
from 9 to 36% by weight (or to 37% by weight) of Ni,
from 1 to 3% by weight of Si,
from 0.1 to 0.3% by weight of N,
from ≥0 to ≤0.15% by weight of C,
from ≥0 to ≤5 4% by weight of Mn,
from ≥0 to ≤4% by weight of Al,
from ≥0 to 0.05% by weight of P,
from ≥0 to 0.05% by weight of S, and,
from ≥0 to 0.1% by weight of one or more rare earth metals, and,
apart from these, Fe and impurities resulting from production, the percentages each being based on the total weight.

The aforementioned group S of possible steels B is described in detail in DE 102005061626.7. Within this group S, preference is given to the following compositions:
from 18 to 26% by weight of Cr,
from 9 to 36% by weight of Ni,
from 1 to 2.5% by weight of Si,
from 0.1 to 0.3% by weight of N,
from ≥0, preferably (independently of the other contents)
from 0.03 to 0.15% by weight of C,
from ≥0 to 3% by weight of Mn,
from ≥0 to 4% by weight of Al,
from ≥0 to 0.05% by weight of P,
from ≥0 to 0.05% by weight of S, and,
from ≥0 to 0.1%, preferably from >0 to 0.1, and more preferably
from 0.03 to 0.08 (in each case independently of all other contents) % by weight of one or more rare earth metals (preferably Ce or Ce and one or more other rare earth metals), and,
apart from these, Fe and impurities resulting from production, the percentages each being based on the total weight (of the steel).

Further preferred compositions within the group S of possible steels B are the following:
from 20 to 25% by weight Cr,
from 9 to 20 or (independently of the other contents) preferably to 15% by weight of Ni,
from 1.4 to 2.5% by weight of Si,
from 0.1 to 0.3% by weight of N,
from ≥0, preferably (independently of the other contents)
from 0.03 to 0.15% by weight of C,
from to ≥0 to 3% by weight of Mn,
from ≥0 to 4% by weight of Al,
from ≥0 to 0.05% by weight of P,
from ≥0 to 0.05% by weight of S, and,
from ≥0 to 0.1, preferably from >0 to 0.1, and more preferably from 0.03 to 0.08 (in each case independently of all other contents) % by weight of one or more rare earth metals (preferably Ce or Ce and one or more other rare earth metals), and,
apart from these, Fe and impurities resulting from production, the percentages each being based on the total weight (of the steel).

Another preferred subgroup of compositions within the group S of possible steels B are the following:
from 20 to 22% by weight of Cr,
from 10 to 12% by weight of Ni,
from 1.4 to 2.5% by weight of Si,
from 0.12 to 0.2% by weight of N,
from ≥0, preferably (independently of all other contents)
from 0.05 to 0.12% by weight of C,
from ≥0 to 1% by weight of Mn,
from ≥0 to 2, preferably (independently of all other contents)
0% by weight of Al,
from ≥0 to 0.045% by weight of P,
from ≥0 to 0.015% by weight of S, and
from ≥0 to 0.1, preferably >0 to 0.1, and more preferably from 0.03 to 0.08 (in each case depending on all other contents) % by weight of one or more rare earth metals, and,
apart from these, Fe and impurities resulting from production, the percentages each being based on the total weight.

Quite generally, it is favorable for all steels B belonging to the group S when the content of N is ≥0.11, better ≥0.12, preferably ≥0.13, more preferably ≥0.14 and even better ≥0.15% by weight.

Particularly favorable steels B within the group S of steels B are those of EN materials numbers 1.4818, 1.4835 and 1.4854, and those of DIN materials numbers 1.4891 and 1.4893. The group S of steels B suitable in accordance with the invention also includes the alloyed stainless steel THERMAX® 4835 from Thyssen Krupp Nirosta GmbH, in D-47794 Krefeld, Germany.

Useful steels A suitable in accordance with the invention and having from 30 to 35% by weight of Ni include in particular the DIN materials 1.4958 and 1.4959.

Further steels suitable in accordance with the invention are the DIN material 1.4941, whose composition may be within the following composition framework
from 17 to 19% by weight of Cr,
from 9 to 12% by weight of Ni,
from ≥0 to 0.8% by weight of Si,
from ≥0 to 0.08 (or ≥0.04 to 0.08) % by weight of C,
from ≥0 to 2% by weight of Mn,
from ≥0 to 0.6% by weight of Mo,
from ≥0 to 0.8% by weight of Ti,
from ≥0 to 0.005% by weight of B,
from ≥0 to 0.05% by weight of P,
from ≥0 to 0.05% by weight of S, and,
apart from these, Fe and impurities resulting from production, the percentages each being based on the total weight,
the DIN material 1.4541 with, for example, the composition
from 17.31% by weight of Cr,
from 10.05% by weight of Ni,
from 0.51% by weight of Si,
from 0.017% by weight of N,
from 0.042% by weight of C,
from 1.17% by weight of Mn,
from 0.025% by weight of P,
from <0.00005% by weight of S,
from 0.29% by weight of Ti, and,
apart from these, Fe and impurities resulting from production, the percentages each being based on the total weight (test certificate from Sterling Tubes),
and the DIN material 1.4948 whose composition may lie within the following composition framework:
from 17 to 19% by weight of Cr,
from 8 to 11% by weight of Ni,
from ≥0 to 0.8% by weight of Si,
from ≥0 to 0.11% by weight of N,
from 0.04 to 0.08% by weight of C,
from ≥0 to ≤2.0% by weight of Mn,
from ≥0 to 0.05% by weight of P,
from ≥0 to 0.05% by weight of S, and, apart from these, Fe and impurities resulting from production, the percentages each being based on the total weight.

For example, the composition of the DIN material 1.4948 may be:
from 18.1% by weight of Cr,
from 8.3% by weight of Ni,
from ≥0 to 0.8% by weight of Si,
from ≥0 to 0.11% by weight of N,
from 0.05% by weight of C,
from ≥0 to ≤2.0% by weight of Mn,
from ≥0 to 0.05% by weight of P,
from ≥0 to 0.05% by weight of S, and,
apart from these, Fe and impurities resulting from production, the percentages each being based on the total weight.

In other words, particularly suitable steels A are encompassed under the composition framework
from 16 to 19% by weight of Cr,
from 8 to 14% by weight of Ni,
from ≥0 to ≤0.8% by weight of total amount of Si and Al,
from ≥0 to 0.2% by weight of N,
from ≥0 to 0.1% by weight of C,
from ≥0 to 3% by weight of Mo, or from ≥0 to 2.0 (or to 1.5) % by weight of Mn,
from ≥0 to 0.8% by weight of Ti,
from ≥0 to 0.05% by weight of B,
from ≥0 to 0.05% by weight of P,
from ≥0 to 0.05% by weight of S, and
apart from these, Fe and impurities resulting from production, the percentages each being based on the total weight.

A further steel suitable in accordance with the invention is the DIN material 1.4949 which may lie within the following composition framework:
from 17 to 19% by weight of Cr,
from 9.5 to 11.5% by weight of Ni,
from ≥0 to 0.8% by weight of Si,
from 0.1 to 0.18% by weight of N,
from ≥0 to 0.04% by weight of C,
from ≥0.2 to 0.5% by weight of Mo,
from ≥0 to 2% by weight of Mn,
from ≥0 to 0.035% by weight of P,
from ≥0 to 0.015% by weight of S, and,
apart from these, Fe and impurities resulting from production, the percentages each being based on the total weight.

Further steels A suitable in accordance with the invention may lie within the following composition framework:
from 15 to 17.5% by weight of Cr,
from 12 to 17.5% by weight of Ni,
from 0.3 to 0.6% by weight of Si,
from ≥0 to 0.14% by weight of N,
from 0.04 to 0.1% by weight of C,
from ≥0 to 2% by weight of Mo,
from ≥0 to 1.5% by weight of Mn,
from 10 times the C content to 1.2% by weight of Nb,
from 0.6 to 0.85% by weight of V,
from ≥0 to 0.035% by weight of P,
from ≥0 to 0.015% by weight of S, and,
apart from these, Fe and impurities resulting from production, the percentages each being based on the total weight.

In other words, useful inventive steels A also include DIN materials 1.4961, 1.4981 and 1.4988.

In all steels A to be used in accordance with the invention, the Si content is, preferably in accordance with the invention, ≤0.7% by weight or ≤0.6% by weight, better ≤0.5% by weight or ≤0.4% by weight, even better ≤0.3% by weight, even more preferably ≤0.2% by weight or ≤0.1% by weight, and at best steels A to be used in accordance with the invention comprise no Si.

In complete correspondence with this, the Al content in all steels A to be used in accordance with the invention is, preferably in accordance with the invention, ≤0.7% by weight or ≤0.6% by weight, better ≤0.5% by weight or ≤0.4% by weight, even better ≤0.3% by weight, even more preferably ≤0.2% by weight or ≤0.1% by weight, and at best steels A to be used in accordance with the invention comprise no Al.

The notched impact resistance of the steels A to be used in accordance with the invention is generally ≥50 J.

Both the steels A and the steels B comprise quite generally frequently ≥0.01% by weight, or ≥0.02% by weight, or ≥0.03% by weight of C, especially those mentioned in this document.

Both the steels A and the steels B generally comprise minimum contents of P and of S. In all steel (A, B) compositions listed in this document, the following contents apply appropriately in accordance with the invention:
from ≥0 to ≤0.035% by weight of P and
from ≥0 to 0.02% by weight of S.

Preferably in accordance with the invention, the (pipe)lines which conduct the at least one starting gas stream toward the reaction chamber and the at least one product gas stream away from the reaction chamber are also manufactured from the composite material to be used in accordance with the invention. These tubes (especially those conducting the product gas away) may, though, in principle also be manufactured only from steels of DIN materials numbers 1.4891, or 1.4893 or 1.4910, or 1.4941, or 1.4541 or 1.4841. The use of inventive composite material is of increased relevance especially when reaction gas which has a temperature of ≥450° C. and the working pressure of >1 atm comes into contact with material.

For proper and reliable operation, the aforementioned (pipe)lines are preferably equipped with devices for compensating longitudinal expansion effects, as can occur, for example, owing to temperature changes, and it is disadvantageous to use compensators which feature a lateral mode of action.

These compensators which generally have a multilayer design may be manufactured from the same material as the pipeline itself. However, particularly advantageous embodiments are those with (generally: gas-permeable rigid inner tube and gas-impermeable elastic outer sleeve (gas-impermeable elastic outer tube)) an inner tube part, preferably manufactured from the composite material to be used in accordance with the invention, which is in contact with the gas to be conducted and appropriately has a gas-permeable expansion joint and an external, gas-impermeable, elastic, corrugated part which is manufactured at least partly from an especially mechanically and thermally stressable material, for example material 1.4876 (designation according to VdTÜV-Wb 434) or 1.4958/1.4959 (designation according to DIN 17459) or INCOLOY® 800H or 800HT, or nickel-base alloy 2.4816 (alternative designation Alloy 600) or 2.4851 (alternative designation Alloy 601).

In principle, the shell (E) for the reaction chamber, just like the supply and withdrawal pipelines, may also be manufactured from nickel-base alloy 2.4642 (alternative designation Alloy 690 or Inconel H 690).

The composite material to be used in accordance with the invention is suitable in particular for those processes according to the invention in which the reaction temperatures and/or catalyst regeneration temperatures are from ≥400 to 900° C., or from ≥500 to 800° C., or from ≥550 to ≤750° C., or from ≥600 to ≤700° C.

Otherwise, steels A, B to be used in accordance with the invention are commercially available or producible in a manner known per se; see, for example, the remarks in Enzyklopädie Naturwissenschaften und Technik [Encyclopedia of natural sciences and technology], Verlag moderne Industrie, 1976, under the headings "Stahlbegleiter" [Steel companions], "Eisen" [Iron] and "Eisen und Stahl" [iron and steel], or Ullmanns Encyclopädie der technischen Chemie, Verlag Chemie, 4th edition, volume 3, 1973, Verfahrenstechnik II und Reaktionsapparate [Process technology II and reaction apparatus], chapter "Werkstoffe in der chemischen Industrie" [Materials in the chemical industry].

Of course, composite material to be used in accordance with the invention may also comprise steel B, on its side in contact with the reaction chamber, in alonized, alitized and/or aluminized form. When the alonization is damaged, for example, as a result of fabrication, this is not very disadvantageous, given that the inventive advantageousness still comes into effect.

The process according to the invention is advantageous especially when the at least one starting stream comprises steam (for example ≥1% by volume) as an inert diluent gas and/or molecular oxygen (for example ≥0.1 or ≥0.5% by volume) as a reactant. However, it is also advantageous when the at least one starting gas stream comprises steam and/or molecular oxygen as impurities. It is also advantageous when, in the course of the inventive heterogeneously catalyzed partial dehydrogenation, steam is formed as a reaction product. This is especially true when the cycle gas or loop method recommended in WO 03/076370 is employed for the process according to the invention. However, the process according to the invention is particularly advantageous not least when the at least one starting gas stream comprises residual gas which stems from a partial oxidation of dehydrogenated hydrocarbon formed in the process according to the invention connected downstream of the process according to the invention, accompanied by hydrocarbon yet to be dehydrogenated, remains after target product removal from the product gas mixture of the partial oxidation and comprises oxygenate.

Quite generally, the at least one catalyst bed disposed in the reaction chamber may be either a fluidized bed or a moving bed or a fixed bed. Of course, fluidized bed and, for example, fixed bed, or moving bed and fixed bed, may also be present in combination in the reaction chamber. Preferably in accordance with the invention, the at least one catalyst bed of the process according to the invention comprises exclusively fixed catalyst beds.

In this document, the loading of a catalyst bed catalyzing a reaction step with reaction gas should be understood quite generally to mean the amount of reaction gas in standard liters (=l (STP); the volume in liters that the corresponding amount of reaction gas would take up under standard conditions (0° C., 1 atm)) which is conducted through one liter of catalyst bed (for example fixed catalyst bed) per hour. However, the loading may also be based only on one constituent of the reaction gas. In that case, it is the amount of this constituent in l (STP)/l·h which is conducted through one liter of the catalyst bed per hour (pure inert material beds are not counted in a fixed catalyst bed). The loading may also be based only on the amount of catalyst present in one catalyst bed which comprises the actual catalyst diluted with inert material (this is then stated explicitly).

In this document, a full oxidation (combustion) of a dehydrogenated hydrocarbon and/or hydrocarbon to be dehydrogenated is understood to mean that the total amount of carbon present in the hydrocarbon is converted to oxides of carbon (CO, $CO_2$). All different conversions of a dehydrogenated hydrocarbon and/or hydrocarbon to be dehydrogenated with the reactive action of molecular oxygen are encompassed in this document with the term partial oxidation. The additional reactive action of ammonia is a feature of ammoxidation, which is likewise encompassed under the term partial oxidation.

In this document, an inert gas should be understood generally to mean a reaction gas constituent which behaves substantially chemically inertly under the conditions of the appropriate reaction and, each inert reaction gas constituent taken alone, remains chemically unchanged to an extent of more than 95 mol %, preferably to an extent of more than 97 mol % or to an extent of more than 99 mol %. Examples of typically inert diluent gases are, for example, $N_2$, $H_2O$, $CO_2$, noble gases such as Ne and Ar, and mixtures of these gases, etc.

When the process according to the invention is a heterogeneously catalyzed oxydehydrogenation (for example that of propane to propylene), the source used for the molecular oxygen required therefor may be air, pure molecular oxygen or air enriched in molecular oxygen, or other mixtures of molecular oxygen and inert gas. Further possible oxygen sources include nitrogen oxides.

The need to perform the process according to the invention over selective dehydrogenation catalysts in the solid state is caused by the dehydrogenation (splitting of C—H) being kinetically disfavored compared to thermal cleavage or cracking (splitting of C—C). Owing to the selective catalysts and with use of an inventive reaction chamber, by-products such as methane, ethylene and ethane are formed only in minor amounts in the case of an inventive heterogeneously catalyzed dehydrogenation of propane.

In this document, a dehydrogenation catalyst should therefore be understood to mean in particular a shaped body whose longest dimension L (longest direct line connecting two points present on the surface of the shaped body) is from 0.1 or 1 to 30 mm, preferably from 1 to 20 mm and more preferably from 1 to 10 mm or from 1 to 5 mm, and which, in the experiment described below, based on single pass of the reaction gas through the reaction tube, dehydrogenates at least 5 mol % of the propane present in the reaction gas to propylene:

A reaction tube made of steel of EN materials number 1.4835 (a steel B) with a wall thickness of 2 mm and an internal diameter of 35 mm and a length of 80 cm is charged as follows. 50 ml of a bed of the appropriate dehydrogenation catalyst are placed centrally in the reaction tube. Above and below the bed of shaped catalyst bodies, the reaction tube is filled up in each case with a bed of steatite spheres (inert spheres) having a sphere diameter of from 1.5 mm to 2.5 mm. A grid bears the entire bed. From the outside, the reaction tube is kept at a temperature of 550° C. over its entire length. The reaction tube is charged with a mixture of propane and steam in a volume ratio of 2 (propane) to 1 (steam) with a propane loading of the catalyst bed of 1000 l (STP)/l·h. The starting gas stream has been preheated to a temperature of 550° C. Particular preference is given to dehydrogenation catalysts in which the cumulative selectivity of the formation of the ethane, ethylene and methane by-products under the aforementioned boundary conditions is ≤5 mol %, based on converted propane.

An inventive heterogeneously catalyzed oxydehydrogenation can in principle be carried out in such a way as described, for example, in the documents U.S. Pat. No. 4,788,371, CN-A 1073893, Catalysis Letters 23 (1994), 103-106, W. Zhang, Gaodeng Xuexiao Huaxue Xuebao, 14 (1993) 566, Z. Huang, Shiyou Huagong, 21 (1992) 592, WO 97/36849, DE-A 197 53 817, U.S. Pat. Nos. 3,862,256, 3,887,631, DE-A 195 30 454, U.S. Pat. No. 4,341,664, J. of Catalysis 167, 560-569 (1997), J. of Catalysis 167, 550-559 (1997), Topics in Catalysis 3 (1996) 265-275, U.S. Pat. No. 5,086,032, Catalysis Letters 10 (1991), 181-192, Ind. Eng. Chem. Res. 1996, 35, 14-18, U.S. Pat. No. 4,255,284, Applied Catalysis A: General, 100 (1993), 111-130, J. of Catalysis 148, 56-67 (1994), V. Cortés Corberán and S. Vic Bellón (Ed.), New Developments in Selective Oxidation II, 1994, Elsevier Science B.V., p. 305-313, 3$^{rd}$ World Congress on Oxidation Catalysis, R. K. Grasselli, S. T. Oyama, A. M. Gaffney and J. E. Lyons (Ed.), 1997, Elsevier Science B.V., p. 375ff or in DE-A 198 37 520, DE-A 198 37 517, DE-A 198 37 519 and DE-A 198 37 518, using the example of the heterogeneously catalyzed partial oxydehydrogenation of propane. In this case, as already stated, the oxygen source used may, for example, be air. However, the oxygen source used, in addition to inert gas, here frequently has molecular oxygen to an extent of at least 90 mol %, and in many cases molecular oxygen to an extent of at least 95 mol %.

The catalysts suitable for the heterogeneously catalyzed oxydehydrogenation are subject to no particular restrictions. Suitable oxydehydrogenation catalysts are all of those which are known to those skilled in the art in this field and are capable, for example, of oxidizing propane to propylene. In particular, all oxydehydrogenation catalysts mentioned in the aforementioned documents may be used. Suitable catalysts are, for example, oxydehydrogenation catalysts which comprise MoVNb oxides or vanadyl pyrophosphate, if appropriate with promoter. One example of a favorable oxydehydrogenation catalyst is a catalyst which comprises a mixed metal oxide I with Mo, V, Te, O and X as essential constituents, where X is at least one element selected from niobium, tantalum, tungsten, titanium, aluminum, zirconium, chromium, manganese, gallium, iron, ruthenium, cobalt, rhodium, nickel, palladium, platinum, antimony, bismuth, boron, indium, silicon, lanthanum, sodium, lithium, potassium, magnesium, silver, gold and cerium (on this subject, see also EP-A 938463 and EP-A 167109). Further particularly suitable oxydehydrogenation catalysts are the multimetal oxide compositions or catalysts A (referred to in this document as multimetal oxide compositions II) of DE-A-197 53 817 and the catalysts of DE-A 19838312, the multimetal oxide compositions or catalysts A mentioned as preferred in the former document being very particularly favorable. Thus, useful active compositions for an inventive heterogeneously catalyzed oxydehydrogenation include multimetal oxide compositions of the general formula III

$$M^1{}_a Mo_{1-b} M^2{}_b O_x \tag{III}$$

where
$M^1$=Co, Ni, Mg, Zn, Mn and/or Cu,
$M^2$=W, V, Te, Nb, P, Cr, Fe, Sb, Ce, Sn and/or La,
a=0.5-1.5,
b=0-0.5, and
x=a number which is determined by the valency and the frequency of the elements in (III) other than oxygen.

They can be prepared and shaped as described in DE-A 102 45 585.

For a heterogeneously catalyzed oxydehydrogenation of propane for example, the reaction temperature when fresh catalysts are used is preferably in the range from 200 to 600° C., in particular in the range from 250 to 500° C., more preferably in the range from 350 to 440° C. The working pressure is preferably in the range from 0.5 to 10 bar, in particular from 1 to 10 bar, more preferably from 1 to 5 bar. Working pressures above 1 bar, for example from 1.5 to 10 bar, have been found to be particularly advantageous. In general, the heterogeneously catalyzed oxydehydrogenation of propane is effected over a fixed catalyst bed. The latter is appropriately introduced (generally disposed on a gas-permeable grid) into the tubes (the tube wall together with the two tube orifices forms the shell in contact with the reaction chamber; the tube interior is the reaction chamber; the tube wall is preferably manufactured entirely from inventive steel) of a, for example, salt bath-cooled tube bundle reactor, as described, for example, in EP-A 700 893 and in EP-A 700 714 and in the literature cited in these documents. The starting gas stream is fed to the tube inlet. The mean residence time of the reaction gas in the catalyst bed is appropriately from 0.5 to 20 seconds. The ratio of propane to oxygen varies with the desired conversion and the selectivity of the catalyst. It is appropriately in the range from 0.5:1 to 40:1, in particular from 1:1 to 6:1, more preferably from 2:1 to 5:1. In general, the propylene selectivity decreases with increasing propane conversion. Preference is therefore given to carrying out the propane-to-propylene reaction in such a way that relatively low conversions with propane are achieved at high selectivities for propylene. More preferably, the conversion of propane is in the range from 5 to 40 mol %, frequently in the range from 10 to 30 mol %. In this context, the term "propane conversion" means the proportion of propane fed which is converted in single pass of the reaction gas through the tube. In general, the selectivity of propylene formation is from 50 to 98 mol %, more preferably from 80 to 98 mol %, the term "selectivity" meaning the moles of propylene which are obtained per mole of propane converted, expressed as the molar percentage. In the reaction tube, the reaction temperature generally passes through a maximum.

In general, the starting gas stream used in a heterogeneously catalyzed propane oxydehydrogenation comprises from 5 to 95 mol % of propane (based on 100 mol % of starting gas). In addition to propane and oxygen, the starting gas for the heterogeneously catalyzed oxydehydrogenation may also comprise further, especially inert, constituents such as carbon dioxide, carbon monoxide, nitrogen, noble gases, other hydrocarbons, present, for example, in crude propane (the propane source used for the process according to the invention is normally crude propane as recommended, for example, in DE-A 10245585 or DE-A 102005022798), and/or propylene. The heterogeneously catalyzed oxydehydrogenation may also be carried out in the presence of diluents, for example steam.

Any desired reactor sequence known to those skilled in the art may be used to carry out the heterogeneously catalyzed oxydehydrogenation of propane, for example. For example, the heterogeneously catalyzed oxydehydrogenation may be carried out in a single reactor or in a battery of two or more reactors, between which oxygen is fed if appropriate.

As possible constituents, the product gas of an inventive heterogeneously catalyzed propane dehydrogenation may comprise, for example, the following constituents: propylene (as the target product, i.e. as the dehydrogenated hydrocarbon), propane (as the unconverted hydrocarbon to be dehydrogenated), carbon dioxide, carbon monoxide, water, nitrogen, oxygen, ethane, ethene, methane, acrolein, acrylic acid, methacrolein, methacrylic acid, furfurals, ethylene oxide, butane (e.g. n-butane or isobutane), acetic acid, formaldehyde, formic acid, propylene oxide and butenes (e.g. butene-1). Especially the ethane, ethene and methane are possible thermal decomposition products of propane. Typically, a product gas present in an inventive heterogeneously catalyzed propane oxydehydrogenation comprises: from 5 to 10 mol % of propylene, from 0.1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 2 mol % of acetic acid, from 0.01 to 0.05 mol % of formaldehyde, from 1 to 5 mol % of oxygen, from 0.1 to 10 mol % of further constituents mentioned above, and also substantially propane as the remainder, based in each case on 100% product gas.

Heterogeneously catalyzed oxydehydrogenations of hydrocarbons other than propane to be dehydrogenated may be carried out in accordance with the invention in a corresponding manner, as described above for the oxydehydrogenation of propane. Useful such hydrocarbons to be oxydehydrogenated are in particular butane (to butene (in particular isobutane to isobutene) and/or butadiene) and also butenes (to butadiene).

The regeneration of catalysts used for a partial heterogeneously catalyzed oxydehydrogenation of propane, for example, can be undertaken as described for partial oxidation catalysts in the documents DE-A 103 51 269, DE-A 103 50 812 and DE-A 103 50 822.

When the inventive heterogeneously catalyzed partial dehydrogenation is not an oxydehydrogenation, it always includes a conventional heterogeneously catalyzed dehydrogenation, i.e. molecular hydrogen is formed at least as an intermediate and, in the case of an oxidative (conventional) heterogeneously catalyzed partial dehydrogenation, is at least partly combusted in a subsequent step with molecular oxygen to give water.

Useful catalysts for a heterogeneously catalyzed conventional dehydrogenation of hydrocarbons to be dehydrogenated in the process according to the invention are in principle all dehydrogenation catalysts known in the prior art for conventional heterogeneously catalyzed dehydrogenations. They can be divided roughly into two groups, specifically into those which are of oxidic nature (for example chromium oxide and/or aluminum oxide) and into those which consist of at least one generally comparatively noble metal (for example platinum) deposited on a generally oxidic support. The dehydrogenation catalysts which may be used thus include all of those which are recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. Nos. 4,220,091, 5,430,220, 5,877,369, EP-A-0 117 146, DE-A 199 37 196, DE-A 199 37 105, U.S. Pat. Nos. 3,670,044, 6,566,573, 4,788,371, WO-A 94/29021 and DE-A 199 37 107. In particular, the catalyst according to Example 1, Example 2, Example 3 and Example 4 of DE-A 199 37 107 may be used.

These are dehydrogenation catalysts which comprise from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth transition group of the periodic table of the elements, lanthanum and/or tin, with the proviso that the sum of the percentages adds up to 100% by weight.

Generally, the dehydrogenation catalysts may be catalyst extrudates (diameter typically from 0.1 or 1 to 10 mm, preferably from 1.5 to 5 mm; length typically from 1 to 20 mm, preferably from 3 to 10 mm), tablets (preferably the same dimensions as for the extrudates) and/or catalyst rings (external diameter and length in each case typically from 2 to 30 mm or to 10 mm, wall thickness appropriately from 1 to 10 mm, or to 5 mm, or to 3 mm). For a heterogeneously catalyzed dehydrogenation in a fluidized bed (or moving bed), more finely divided catalyst will accordingly be used. Preference is given in accordance with the invention to the fixed catalyst bed.

In general, the dehydrogenation catalysts (especially those recommended in DE-A 199 37107 (especially the exemplary catalysts of this DE-A)) are such that they are capable of catalyzing both the dehydrogenation of the hydrocarbon to be dehydrogenated (e.g. propane) and the combustion of the hydrocarbon to be dehydrogenated (e.g. propane) and of molecular hydrogen. The hydrogen combustion proceeds very much more rapidly over the catalysts both in comparison to the dehydrogenation of the hydrocarbon to be dehydrogenated (e.g. propane) and in comparison to its combustion in the case of a competition situation.

Useful reactor types and process variants for an inventive conventional heterogeneously catalyzed partial dehydrogenation of a hydrocarbon to be dehydrogenated (e.g. propane) are in principle all of those known in the prior art, provided that the reaction chamber in the particular reactor fulfills the inventive profile of requirements. Descriptions of such process variants are present, for example, in all prior art documents cited with regard to the dehydrogenation catalysts and the prior art cited at the outset of this document, and the documents DE 10 2006 017 623.5, 10 2006 015235.2, 10 2005 061 626.7. The same applies to the documents EP-A 1 109 763, U.S. Pat. Nos. 3,308,181, 3,670,044, 4,886,928, 6,566,573, 4,788,371 and WO 94/29021, and the prior art cited in these documents.

A comparatively comprehensive description of processes also suitable for inventive reaction chambers for conventional heterogeneously catalyzed dehydrogenation (nonoxidative or oxidative) is present, for example, in Catalytica® Studies Division, Oxidative Dehydrogenation and Alternative Dehydrogenation Processes, Study Number 41920D, 1993, 430 Ferguson Drive, Mountain View, Calif., 94043-5272 U.S.A.

It is characteristic of the conventional partial heterogeneously catalyzed dehydrogenation of hydrocarbons to be dehydrogenated (e.g. propane) that the dehydrogenation step proceeds endothermically. This means that the heat (energy) required for the attainment of the required reaction temperature has to be supplied to the reaction gas either beforehand and/or in the course of the heterogeneously catalyzed dehydrogenation.

In other words, based on single pass of the at least one starting gas stream through the at least one catalyst bed in the reaction chamber with inventive properties, the reaction chamber can be configured isothermically (externally controlled temperature profile) by controlled heat exchange with, for example, fluid (i.e. liquid or gaseous) heat carriers conducted outside the reaction chamber enclosed by the inventive shell. Corresponding heat exchangers may also be accommodated in the reaction chamber itself.

However, with the same reference basis, it can also be designed adiabatically, i.e. substantially without such controlled heat exchange with (externally) conducted heat carriers (externally uncontrolled temperature profile). In the latter case, the gross thermal character based on single pass through the inventive reaction chamber, by an internally controlled (for example by hydrogen combustion in a subsequent step) temperature profile yet to be described below, may be configured either endothermically (negative) or autothermally (essentially zero) or exothermically (positive).

Typically, an inventive conventional heterogeneously catalyzed partial dehydrogenation of at least one hydrocarbon to be dehydrogenated (for example of propane) requires, as already mentioned, comparatively high reaction temperatures. The achievable conversion is normally restricted by the thermodynamic equilibrium. Typical reaction temperatures are from 300 to 800° C., or from 400 to 700° C. Per molecule of, for example, propane dehydrogenated to propylene, one molecule of hydrogen is obtained. High temperatures and removal of the $H_2$ reaction product shift the equilibrium position toward the target product, as does partial pressure reduction by inert dilution.

In addition, it is typical for conventional heterogeneously catalyzed partial dehydrogenations of at least one hydrocarbon to be dehydrogenated (for example of propane), owing to the high reaction temperatures required, that small amounts of high-boiling high molecular weight organic compounds, up to and including carbon, are formed and are deposited on the catalyst surface, thus deactivating it. In order to minimize this disadvantageous phenomenon, the starting gas which comprises the hydrocarbon to be dehydrogenated (for example the propane) and is to be passed at elevated temperature over the catalyst surface for the conventional heterogeneously catalyzed dehydrogenation can be diluted with steam. Carbon which is deposited is eliminated partly or fully and continuously under the resulting conditions by the principle of coal gasification.

Another means of eliminating deposited carbon compounds consists in flowing a gas comprising oxygen through the dehydrogenation catalyst at elevated temperature from time to time and thus to effectively burn off the deposited carbon. A subsequent reductive treatment with molecular hydrogen normally concludes the catalyst regeneration. However, a certain suppression of the formation of carbon deposits (and thus a lengthening of the catalyst lifetime) is also possible by adding molecular hydrogen to the hydrocarbon to be dehydrogenated in a conventional manner under heterogeneous catalysis (for example propane) before it is conducted over the dehydrogenation catalyst at elevated temperature.

It will be appreciated that the possibility also exists of adding a mixture of steam and molecular hydrogen to the hydrocarbon to be dehydrogenated under heterogeneous catalysis (for example propane), especially for the aforementioned purposes. Addition of molecular hydrogen to the heterogeneously catalyzed dehydrogenation of propane also reduces the undesired formation of allene (propadiene), propyne and acetylene as by-products.

It may therefore be appropriate in accordance with the invention (as already addressed) to carry out the conventional heterogeneously catalyzed hydrocarbon (e.g. propane) dehydrogenation (for example with comparatively low propane (or generally hydrocarbon) conversion) (quasi-)adiabatically. This means that the starting gas will generally first be heated to a temperature of from 400 or 500 to 700° C. (of from 550 to 650° C.) (for example by direct firing of the wall surrounding it). Normally, a single adiabatic pass through at least one catalyst bed disposed in the inventive reaction chamber will be sufficient to achieve the desired conversion, in the course of which the reaction gas will cool by from about 30° C. to 200° C. (depending on conversion and dilution). Presence of steam as a heat carrier is also noticeably advantageous from the point of view of an adiabatic method. The comparatively low reaction temperature enables longer lifetimes of the catalyst bed used.

In principle, an inventive conventional heterogeneously catalyzed hydrocarbon (e.g. propane) dehydrogenation (irrespective of whether conducted adiabatically or isothermally) can be carried out either in a fixed catalyst bed or in a moving bed or fluidized bed.

Suitable catalyst charges for a conventional heterogeneously catalyzed dehydrogenation of a hydrocarbon to be dehydrogenated (e.g. propane) with a comparatively low conversion as described in single pass through the inventive reaction chamber are especially the catalysts disclosed in DE-A 199 37 107, in particular disclosed by way of example, and their mixtures with geometric shaped bodies which are inert with respect to the conventional heterogeneously catalyzed dehydrogenation.

After prolonged operating time, the aforementioned catalysts can be regenerated in a simple manner, for example, by initially passing air (preferably) diluted with nitrogen and/or steam in first oxidative regeneration stages through the (fixed) catalyst bed at an inlet temperature of from 300 to 600° C. (in extreme cases, if appropriate, even to 750° C.), frequently from 400 to 550° C. The catalyst loading with regeneration gas may (based on the total amount of catalyst regenerated) be, for example, from 50 to 10 000 $h^{-1}$ and the oxygen content of the regeneration gas from 0.1 to 25 or from 0.5 to 20% by volume.

In subsequent further oxidative regeneration stages, the regeneration gas used under otherwise identical regeneration conditions may be air. Appropriately from an application point of view, it is recommended to flush the catalyst with inert gas (e.g. $H_2O$, $N_2$, or a mixture thereof) before it is regenerated.

Subsequently, it is generally advisable to regenerate reductively with pure molecular hydrogen or with molecular hydrogen diluted with inert gas (preferably steam and/or nitrogen) (the hydrogen content should be ≥1% by volume) under otherwise identical conditions.

A conventional heterogeneously catalyzed hydrocarbon (e.g. propane) dehydrogenation in the process according to the invention may be operated both at low (≤30 mol %) and at high (≥30 mol %) conversion of hydrocarbon to be dehydrogenated (e.g. propane) in the inventive reaction chamber at catalyst loadings (based on the total amount of catalyst used) both with starting gas and with hydrocarbon to be dehydrogenated present therein (e.g. propane) of from 100 to 10 000 $H^{-1}$, frequently from 300 to 5000 $h^{-1}$, i.e. in many cases from 500 to 3000 $h^{-1}$.

In a particularly elegant manner, a conventional inventive heterogeneously catalyzed dehydrogenation of at least one hydrocarbon to be dehydrogenated (e.g. propane) can be implemented in an inventive tray reaction chamber (both at dehydrogenation conversions of ≤30 mol % and >30 mol % (e.g. 40 mol %, or 50 mol %)).

Such an inventive tray reaction chamber comprises more than one catalyst bed catalyzing the dehydrogenation in spatial succession. The catalyst bed number may, for example, be from 1 to 20, appropriately from 2 to 8, but also from 3 to 6. The catalyst beds are preferably arranged in radial or axial succession. From an application point of view, it is appropriate to use the fixed catalyst bed type in such a tray reaction chamber.

In the simplest case, the fixed catalyst beds are arranged in the reaction chamber axially or in the annular gaps of concentric cylindrical grids. However, it is also possible to arrange the annular gaps in the reaction chamber in segments one above the other and to conduct the gas, after it has passed radially through one segment, into the next segment above it or below it.

Appropriately, the reaction gas (starting gas), on its way from one catalyst bed to the next catalyst bed, is subjected to intermediate heating in the tray reaction chamber, for example by passing it over heat exchanger ribs heated with hot gases or by passing it through pipes heated with hot combustion gases or heat exchanger plates heated with hot gases.

When the process according to the invention in the tray reaction chamber is otherwise operated adiabatically, it is sufficient for dehydrogenation conversions (e.g. propane conversion) of ≤30 mol %, especially when using the catalysts described in DE-A 199 37 107, especially those of the exemplary embodiments, to conduct the starting gas into the reaction chamber preheated to a temperature of 400 or 450 to 550° C. (preferably from 400 to 500° C.) and to keep it at least within this temperature range inside the tray reaction chamber. This means that the entire inventive dehydrogenation can thus be implemented, at least with fresh catalysts, at comparatively moderate temperatures, which is found to be particularly favorable for the lifetime of the fixed catalyst beds between two regenerations.

It is even more elegant to carry out a conventional heterogeneously catalyzed dehydrogenation in the inventive reaction chamber (as likewise already addressed) substantially autothermally, i.e. to carry out the intermediate heating outlined above by a direct route (autothermal method).

To this end, a limited amount of molecular oxygen can be added advantageously to the reaction gas on its way through the inventive reaction chamber, for example after it has flowed through the first catalyst bed and between the downstream catalyst beds. Depending on the dehydrogenation catalyst used, limited combustion of the hydrocarbons present in the reaction gas, any coke or coke-like compounds already deposited on the catalyst surface and/or of hydrogen which has been formed in the course of the conventional heterogeneously catalyzed dehydrogenation (for example of a propane dehydrogenation) and/or has been added to the reaction gas can thus be brought about (it may also be appropriate from an application point of view to insert catalyst beds in the tray reaction chamber which have been charged with catalyst which specifically (selectively) catalyzes the combustion of hydrogen (and/or of hydrocarbon) (useful such catalysts include, for example, those of the documents U.S. Pat. Nos. 4,788,371, 4,886,928, 5,430,209, 5,530,171, 5,527, 979 and 5,563,314; for example, such catalyst beds may be accommodated in the tray reaction chamber in alternation to the beds comprising dehydrogenation catalyst). The heat of reaction released thus allows (quasi-adiabatic reactor configuration), in a quasi-autothermal manner, a virtually isothermal (internal temperature control) operating mode of the heterogeneously catalyzed (e.g. propane) dehydrogenation. With increasing selection of the residence time of the reaction gas mixture in the catalyst bed, a (e.g. propane) dehydrogenation is thus possible at decreasing or substantially constant temperature, which enables particularly long lifetimes between two regenerations (instead of a tray reactor, it is also possible in an equivalent manner to use a series connection of a number of reactors having an inventive shell E which corresponds to the aforementioned number of trays, and to undertake the feeding of oxygen between successive reactors in each case. The number of reactors thus connected may be, for example, "three" or "two", or "four". In general, every single one of these reactors will have one or at most two fixed catalyst beds).

By virtue of subsequent combustion, carried out as described, of molecular hydrogen formed in the course of the dehydrogenation, a nonoxidative conventional heterogeneously catalyzed dehydrogenation becomes an oxidative conventional heterogeneously catalyzed dehydrogenation in the sense of the present application.

In general, oxygen feeding as described above should be undertaken such that the oxygen content of the reaction gas, based on the amount of hydrocarbon to be dehydrogenated and dehydrogenated hydrocarbon present therein (e.g. propane and propylene) is from 0.01 or 0.5 to 30% by volume. Useful oxygen sources are either pure molecular oxygen or oxygen diluted with inert gas, for example CO, $CO_2$, $N_2$, noble gases, but in particular also air. An alternative oxygen source may be nitrogen oxides. The resulting combustion gases generally have an additional diluting effect and thus promote the heterogeneously catalyzed (e.g. propane) dehydrogenation.

The isothermicity of a conventional heterogeneously catalyzed (e.g. propane) dehydrogenation can be improved further by incorporating closed (for example tubular) internals in the tray reaction chamber which have favorably, but not necessarily, been evacuated before filling in the spaces between the catalyst beds. Such internals may also be placed into the particular catalyst bed. These internals comprise suitable solids or liquids which evaporate or melt above a certain temperature and consume heat as they do so, and, when the temperature falls below this value, condense again and release heat as they do so.

Another means of heating the starting gas or the starting gas stream for a conventional heterogeneously catalyzed (e.g. propane) dehydrogenation in the inventive reaction chamber to the required reaction temperature is to combust a portion of the hydrocarbon to be dehydrogenated (e.g. of the propane) and/or $H_2$ present therein by means of the molecular oxygen present in the starting gas on entry into the reaction chamber (for example over suitable specific combustion catalysts, for example by simply passing it over and/or passing it through), and bringing about the heating to the reaction temperature desired (for the dehydrogenation) by means of the heat of combustion thus released. The resulting combustion products, such as $CO_2$, $H_2O$ and the $N_2$ which may accompany the molecular oxygen required for the combustion, are advantageous inert diluent gases.

The aforementioned hydrogen combustion can be implemented in a particularly elegant manner as described in WO 03/076370 or DE-A 102 11 275. In other words, in a process for continuous conventional oxidative heterogeneously catalyzed partial dehydrogenation of hydrocarbon to be dehydrogenated (e.g. in propane) in the inventive reaction chamber, in which at least one starting gas stream comprising at least one hydrocarbon to be dehydrogenated (e.g. propane), molecular oxygen, molecular hydrogen and, if appropriate, steam is fed continuously to the reaction chamber, in the reaction chamber, the at least one hydrocarbon to be dehydrogenated is conducted through at least one catalyst bed disposed in the reaction chamber, over which molecular hydrogen and, at least partially, at least one dehydrogenated hydrocarbon (e.g. propylene) are formed by conventional heterogeneously catalyzed dehydrogenation, further gas comprising molecular oxygen is added if appropriate to the reaction gas on its way through the reaction chamber after it has entered the inventive reaction chamber, the molecular oxygen in the molecular hydrogen present in the reaction gas in the reaction chamber is oxidized at least partly to steam, and at least one product gas stream which comprises molecular hydrogen, steam, dehydrogenated hydrocarbon (e.g.

propylene) and hydrocarbon to be dehydrogenated (e.g. propane) is withdrawn continuously from the reaction chamber, wherein the at least one product gas stream withdrawn from the inventive reaction chamber is divided into two portions of identical composition and one of the two portions is recycled as dehydrogenation cycle gas into the at least one starting gas stream fed to the inventive reaction chamber, and the other portion is used further in another way (for example for the purpose of a heterogeneously catalyzed partial oxidation of dehydrogenated hydrocarbon formed in the reaction chamber).

For example, the product gas of an inventive, oxidative or nonoxidative heterogeneously catalyzed dehydrogenation of propane to propylene may have the following contents from 25 to 60% by volume of propane,
from 8 to 25% by volume of propylene,
from ≥0 to 25% by volume of $H_2$ and
from ≥0 to 30% by volume of $CO_2$.

In the above remarks, propane has always been mentioned in individualized form as the hydrocarbon to be dehydrogenated under heterogeneous catalysis in a conventional, nonoxidative or oxidative manner. Of course, the procedures described can also be applied to all other compounds listed as hydrocarbons to be dehydrogenated at the outset of this document. In particular, mention should be made among these once again of butane (to butene and/or butadiene; especially isobutane to isobutene) and of butenes to butadiene.

Quite generally, the at least one starting gas stream of an inventive, oxidative or nonoxidative heterogeneously catalyzed dehydrogenation generally comprises ≥5% by volume of the hydrocarbon to be dehydrogenated (e.g. propane). In addition, it may comprise, for example:

a) $N_2$ and $H_2O$;
b) $N_2$, $O_2$ and $H_2O$;
C) $N_2$, $O_2$, $H_2O$ and $H_2$;
d) $N_2$, $O_2$, $H_2O$, $H_2$ and $CO_2$;
e) $N_2$, $O_2$, $H_2O$, $H_2CO_2$ and CO.

As already mentioned, the process according to the invention will in many cases be followed by a process for heterogeneously catalyzed partial oxidation of dehydrogenated hydrocarbon obtained (for example propylene to acrolein and/or acrylic acid), preferably accompanied by unconverted hydrocarbon to be dehydrogenated (e.g. propane) as an inert gas. The product gas stream withdrawn (continuously) from the inventive reaction chamber will be used as such or after removal of at least a portion of its constituents (e.g. $H_2$, $H_2O$, $N_2$, etc.) other than the dehydrogenated hydrocarbon (e.g. propylene) and the (unconverted) hydrocarbon to be dehydrogenated (e.g. propane) to charge at least one oxidation reactor, and the dehydrogenated hydrocarbon present in the charge gas mixture (e.g. propylene) will be subjected to a selective heterogeneously catalyzed partial gas phase oxidation with molecular oxygen to give a product gas mixture B comprising (partial oxidation product) target product (for example acrolein or acrylic acid or a mixture thereof), and also generally unconverted hydrocarbon to be dehydrogenated (e.g. propane), excess molecular oxygen and, if appropriate, unconverted hydrocarbon to be dehydrogenated (e.g. propylene).

In a downstream separation zone B, target product (for example acrolein or acrylic acid or a mixture thereof) present in product gas mixture B will be removed and, from the remaining residual gas comprising unconverted hydrocarbon to be dehydrogenated (e.g. propane), molecular oxygen and, if appropriate, unconverted dehydrogenated hydrocarbon (e.g. propylene), at least a portion comprising unconverted hydrocarbon to be dehydrogenated (e.g. propane) and, if appropriate, unconverted molecular oxygen and, if appropriate, unconverted dehydrogenated hydrocarbon (e.g. propylene) will be recycled into the process according to the invention as partial oxidation cycle gas (for example as a constituent of the starting gas stream).

When the process according to the invention (but also otherwise) is, for example, an oxidative conventional heterogeneously catalyzed partial dehydrogenation of propane to propylene, and the partial oxidation which follows is that of propylene to acrolein or to acrylic acid or to a mixture thereof, the at least one starting gas stream fed to the inventive reaction chamber may comprise, for example, as significant contents:

from ≥0 to 20 or to 10, frequently from 0 to 6% by volume of propylene,
from ≥0 to 1, in many cases from 0 to 0.5, frequently from 0 to 0.25% by volume of acrolein,
from ≥0 to 0.25 (or to 0.4), in many cases from 0 to 0.05, frequently from 0 to 0.03% by volume of acrylic acid,
from ≥0 to 20 or to 5, in many cases from 0 to 3, frequently from 0 to 2% by volume of $CO_x$,
from 5 to 50, preferably from 20 to 40% by volume of propane,
from 20 or 30 to 80, preferably from 50 to 70% by volume of nitrogen,
from ≥0 to 5, preferably from 1.0 to 2.0% by volume of oxygen,
from ≥0 to 20, preferably from 5.0 to 10.0% by volume of $H_2O$, and
from ≥0, frequently from ≥0.01, often from ≥0.05 to 10, preferably from 1 to 5% by volume of $H_2$.

Acetic acid may also be present in small amounts (approximately comparable to the possible acrylic acid contents).

Typically, target product (for example acrylic acid) is removed from product gas mixture B by converting the target product (for example the acrylic acid) into the condensed phase. This can be done by absorptive and/or condensative (cooling) measures. Useful absorbents in the case of acrylic acid as the target product are, for example, water, aqueous solutions or high-boiling ($T_{boil}>T_{boil}$ of acrylic acid at 1 atm), especially hydrophobic, organic solvents. More preferably, the conversion into the condensed phase in the case of acrylic acid is effected by fractional condensation of product gas mixture B. Preference is given to effecting the absorptive and/or condensative conversion of acrylic acid from product gas mixture B into the condensative phase in columns comprising separating internals, in which the product gas mixture is normally conducted ascending from the bottom upward. The absorbent is generally introduced at the top of the column, at which the residual gas is normally released from the column.

The further removal of the acrylic acid from the condensed phase is effected generally in the desired purity using at least one thermal separation process. This is understood to mean those processes in which at least two different substance phases (for example liquid/liquid; gaseous/liquid; solid/liquid; gaseous/solid, etc.) are obtained and contacted with one another. Owing to the gradients existing between the phases, heat and mass transfer takes place between them and ultimately causes the desired separation (removal). The term "thermal separation process" reflects that it requires either the withdrawal or the supply of heat to obtain the formation of the substance phases and/or that the withdrawal or the supply of thermal energy promotes or maintains the mass transfer.

Preferably in accordance with the invention, the at least one thermal separation process comprises at least one crystallizative removal from liquid phase. Appropriately in accordance with the invention, the at least one crystallizative removal of acrylic acid is a suspension crystallization, and the suspension crystals are advantageously washed with molten crystals which have been removed beforehand and washed in a wash column (a gravimetric, or a mechanical, or a hydraulic wash column; preference is given in accordance with the invention to the latter). Otherwise, useful thermal separation processes are, for example, extractive, desorptive, crystallizative, rectificative, azeotropically distillative, azeotropically rectificative, distiltative and/or stripping processes. In general, pure acrylic acid will be obtained by employing combinations of different thermal separation processes of those mentioned.

The removal of acrylic acid described can be followed by a process for free-radical polymerization (especially for preparing water-superabsorbent polyacrylic acids and/or their partly or fully neutralized alkali metal (preferably Na) salts), in which acrylic acid removed is polymerized free-radically to prepare polymers.

It is also possible for the removal of acrylic acid described to be followed by a process for preparing acrylic esters, in which removed acrylic acid is esterified with alcohols (preferably alkanols, more preferably $C_1$- to $C_{12}$-alkanols) (generally under acid catalysis).

The process for esterification may in turn be followed by a process for free-radical polymerization, in which acrylic ester thus prepared is polymerized.

Disregarding the inventive peculiarity of the inventive reaction chamber, processes according to the invention for preparing propylene from propane as the propylene source for partial oxidations thereof to prepare acrolein and/or acrylic acid are known, including a cycle gas method of oxidation cycle gas and, if appropriate, dehydrogenation cycle gas. For example, descriptions of such multistage processes can be found in the documents DE-A 10 2005 022 798, DE 10 2006 024 901.1, DE-A 102 46 119, DE-A 102 45 585, DE-A 10 2005 049 699, DE-A 10 2004 032 129, DE-A 10 2005 013 039, DE-A 10 2005 010 111, DE-A 10 2005 009 891, DE-A 102 11 275, EP-A 117 146, U.S. Pat. No. 3,161,670, DE-A 33 13 573, WO 01/96270, DE-A 103 16 039, DE-A 10 2005 009 885, DE-A 10 2005 052 923, DE-A 10 2005 057 197, WO 03/076370, DE-A 102 45 585, DE-A 22 13 573, U.S. Pat. No. 3,161,670 and the prior art cited in these documents. DE-A 102 19 686 discloses the corresponding procedure in the case of preparation of methacrolein and/or methacrylic acid.

Detailed descriptions of absorptive and/or condensative processes for converting acrylic acid from a product gas mixture B into the condensed phase can likewise be found in the prior art. This includes the documents DE-A 103 36 386, DE-A 196 31 645, DE-A 195 01 325, EP-A 982 289, DE-A 198 38 845, WO 02/076917, EP-A 695 736, EP-A 778 225, EP-A 1 041 062, EP-A 982 287, EP-A 982 288, US-A 2004/0242826, EP-A 792 867, EP-A 784 046, EP-A 695 736 (especially absorptive) and WO 04/035514, DE-A 199 24 532, DE-A 198 14 387, DE-A 197 40 253, DE-A 197 40 252 and DE-A 196 27 847 (especially condensative).

In addition, descriptions of such absorptive and/or condensative removals of acrylic acid from product gas mixtures B can also be found in the documents EP-A 1 338 533, EP-A 1 388 532, DE-A 102 35 847, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 195 01 325, DE-A 102 47 240, DE-A 197 40 253, EP-A 695 736, EP-A 1 041 062, EP-A 117 146, DE-A 43 08 087, DE-A 43 35 172, DE-A 44 36 243, DE-A 103 32 758 and DE-A 199 24 533. In principle, however, it is also possible to proceed as described in DE-A 103 36 386, DE-A 101 15 277, DE-A 196 06 877, EP-A 920 408, EP-A 1 068 174, EP-A 1 066 239, EP-A 1 066 240, WO 00/53560, WO 00/53561, DE-A 100 53 086, WO 01/96271, DE-A 10 2004 032 129, WO 04/063138, WO 04/35514, DE-A 102 43 625 and DE-A 102 35 847.

When the hydrocarbon to be dehydrogenated for the process according to the invention is propane, it will preferably be fed to the at least one starting gas stream as a constituent of crude propane in accordance with the teaching of DE-A 102 45 585.

Generally, the at least one starting gas stream will comprise hydrocarbon to be dehydrogenated at least to an extent of 5% by volume. Frequently, this proportion by volume will be at values on a corresponding basis of ≥10% by volume, often ≥15% by volume and usually ≥20% by volume or ≥25% by volume, or ≥30% by volume. In general, this proportion by volume, however, will be at values on the same basis of ≤90% by volume, usually ≤80% by volume and often ≤70% by volume. The above data apply especially in the case of propane as the hydrocarbon to be dehydrogenated and propylene as the dehydrogenated hydrocarbon. Of course, they also apply where isobutane is the hydrocarbon to be dehydrogenated and isobutene is the dehydrogenated hydrocarbon.

Remarkably, for the performance of an inventive conventional (oxidative or nonoxidative) heterogeneously catalyzed dehydrogenation, especially for an adiabatic operating mode, the interior of a simple shaft furnace ("shaft furnace reactor") is sufficient as the at least one inventive reaction chamber which comprises at least one catalyst bed (for example the at least one fixed catalyst bed) and is flowed through axially and/or radially by the starting gas stream. A particularly preferred embodiment of such a reactor is described by DE 10 2006 017 623.5 and 10 2006 015 235.2.

In the simplest case, it is, for example, a substantially cylindrical vessel whose internal diameter is from 0.1 to 10 m, possibly from 0.5 to 5 m, and in which the at least one fixed catalyst bed is placed on a support device (for example a grid). The reaction chamber charged with catalyst, whose inventive shell in adiabatic operation is additionally thermally insulated against its environment by application of suitable insulating materials (for example glass wool), is appropriately flowed through axially with the hot starting gas stream comprising the hydrocarbon to be dehydrogenated (e.g. the propane). The catalyst geometry may be either spherical or annular or strand-shaped. Since the reaction chamber in the case just described can be implemented by a very inexpensive apparatus, all catalyst geometries which have a particularly low pressure drop are preferable. These are in particular catalyst geometries which lead to a large cavity volume or are structured, for example monoliths or honeycombs. To implement radial flow of the reaction gas comprising the hydrocarbon to be dehydrogenated (e.g. the propane), the inventive reaction chamber may, for example, comprise two concentric cylindrical grids and the catalyst bed may be disposed in their annular gap. In the adiabatic case, the shell which encloses it (the jacket) would, if appropriate, in turn be thermally insulated. In the case of a substantially cylindrical shaft furnace flowed through axially, it is advantageous for the process according to the invention in the case of an adiabatic operating mode when the dimension A of the reaction chamber at right angles to the cylindrical axis is at least 5 times, preferably at least 10 times and more preferably at least 15 times the bed height S of the at least one catalyst bed in axial direction. In general, the aforementioned ratio of A:S will, however, be ≤200, typically ≤150 and usually ≤100.

Against the background of the statements above, the present invention comprises, as part of the inventive subject matter, especially a (material) shell E which encloses an interior I (the reaction chamber) and has at least one first orifice O1 for feeding at least one gas stream (material stream) S into the interior I and at least one second orifice O2 for removal A (withdrawal) of a gas stream (material stream) S fed to the interior I beforehand via the at least one first orifice OO1 from the interior I, the shell E being manufactured from a composite material which consists, on its side B in contact with the interior I, of steel B of the following elemental composition:

from 18 to 30% by weight of Cr,
from 9 to 37% by weight (or,
independently of all other contents,
to 36% by weight) of Ni,
from 1 to 4% by weight (or to
3% by weight) of Si,
from ≥0 to 4% by weight of Al,
from ≥0 to 0.3% by weight of N,
from ≥0 to 0.15% by weight of C,
from ≥0 to 4% by weight of Mn,
from ≥0 to 0.05% by weight of P,
from ≥0 to 0.05% by weight of S, and
from ≥0 to 0.1% by weight of one or more rare earth metals, and
apart from these, Fe and impurities resulting from production, the percentages each being based on the total weight, with the proviso that the steel B, on its side A facing away from the interior I, is plated either directly or via an intermediate layer of copper, or of nickel, or of copper and nickel, onto steel A of the elemental composition from 15 to 20% by weight of Cr,
from 6 to 18% by weight
(frequently to 16% by weight) of Ni,
from ≥0 to 0.8% by weight of Si,
from ≥0 to 0.8% by weight of Al,
from ≥0 to 0.3% by weight of N,
from ≥0 to 0.15% by weight of C,
from ≥0 to 4% by weight of Mo,
from ≥0 to 2 (or to 1.5) %
by weight of Mn,
from ≥0 to 0.5% by weight of Ti,
from ≥0 to 1.2% by weight,
or to 0.5% by weight, of Nb,
from ≥0 to 0.9% by weight of V,
from ≥0 to 0.1% by weight of B,
from ≥0 to 0.05% by weight of P,
from ≥0 to 0.05% by weight of S, and
apart from these, Fe and impurities resulting from production, the percentages each being based on the total weight, or of the elemental composition
from 19 to 23% by weight of Cr,
from 30 to 35% by weight of Ni,
from ≥0 to 1% by weight of Co,
from ≥0 to 1% by weight of Si,
from 0.15 to 0.7% by weight of Al,
from ≥0 to 0.12% by weight of C,
from ≥0 to 2.0% by weight of Mn,
from ≥0 to 0.75% by weight of Cu,
from 0.15 to 0.7% by weight of Ti,
from ≥0 to 0.05% by weight of P,
from ≥0 to 0.05% by weight of S, and
apart from these, Fe and impurities resulting from production, the percentages each being based on the total weight.

Advantageously, the Si content in the latter steel A too will be ≤0.8% by weight. Moreover, the Fe content in the above latter steel A is preferably at least 39.5% by weight. It is also advantageous when the sulfur content in the DIN material 1.4876 is ≥0 and ≤0.15% by weight. The C content of the same material is advantageously and ≤0.1% by weight. Moreover, the P content of the same material is advantageously from ≥0 to ≤0.03% by weight. The sum of Ni and Co in the aforementioned material is advantageously from 30 to 34% by weight.

All statements made earlier in this document on the shell (E), the steels A, B and the intermediate layer of Cu and/or Ni in the context of the process according to the invention also apply to the (material) shell E which encloses the interior I.

In other words, for example, the total amount of impurities resulting from production in the steels A, B of the shell E is, advantageously in accordance with the invention, quite generally and on the same basis, ≤0.1% by weight, preferably ≤0.75% by weight, more preferably ≤0.5% by weight and most preferably ≤0.25% by weight. In general, the entire amount of impurities resulting from production in the particular steel A, B will, however, be ≥0.1 by weight. Preferably in accordance with the invention, the rare earth metal of a steel B is Ce. Preferably in accordance with the invention, a steel B has from ≥0 to 0.1% by weight of Ce or Ce and one or more rare earth metals other than Ce (especially La, Nd and/or Pr).

The interior I of all shells E is suitable, after the introduction of at least one catalyst bed comprising dehydrogenation catalyst, for performing the process according to the invention (especially those for adiabatic heterogeneously catalyzed conventional nonoxidative or oxidative dehydrogenation of propane to propylene).

Advantageously in accordance with the invention, the volume of the interior I (calculated empty) is from 5 $m^3$ to 500 $m^3$, often 10 $m^3$ to 400 $m^3$, frequently from 20 $m^3$ to 300 $m^3$, in many cases from 30 $m^3$ to 200 $m^3$, or from 50 $m^3$ to 150 $m^3$. Possible individual values are thus, for example, 150 $m^3$, 160 $m^3$, 170 $m^3$, 180 $m^3$, 190 $m^3$ and 200 $m^3$.

Of course, useful steels A, B for the steels A, B of the shells E also include all others which are usable in accordance with the invention and have already been mentioned in this document, and in the classification of preference already given above in this document. Advantageously, the steel B is alonized, alitized and/or aluminized on its side in contact with the interior I. The statements made previously on the thickness of the steels A, B and of the intermediate layer of Cu and/or Ni are also valid in connection with the shell E.

In particular, the present invention relates to shells E whose interior I comprises at least one catalyst suitable for a heterogeneously catalyzed partial dehydrogenation of a hydrocarbon to be dehydrogenated (dehydrogenation catalyst). Useful such catalysts are in particular all dehydrogenation catalysts detailed in this document.

The amount of catalyst present in the interior of the shell E may be from 100 kg to 500 t (metric tons) or from 200 kg to 400 t, or from 300 kg to 300 t, or from 400 kg to 200 t, or from 500 kg to 150 t, or from 1 t to 100 t, or from 10 t to 80 t, or from 20 t to 60 t. In this context, any inert shaped bodies which exclusively dilute the catalysts are not counted.

The present invention further relates to shells E whose interior I comprises at least one support grid (preferably at least two concentric grids). Advantageously, the shell E has (comprises) an annular (hollow cylindrical) segment R (or such a section) (in which case the ring interior $I_R$ forms part of the interior I).

If D is half of the difference between the external diameter A (calculated without outer thermal insulation) and the internal diameter of the annular segment R, the ratio $V_1$ of D to A is, preferably in accordance with the invention, from 1:10 to 1:1000, in many cases from 1:20 to 1:800, often from 1:30 to 1:600, in many cases from 1:40 to 1:500, or from 1:50 to 1:400, or from 1:60 to 1:300, but in many cases also from 1:70 to 1:250 (or 200), or from 1:80 to 1:150.

The ratio $V_2$ of the height H (the separation of the two parallel circular planes delimiting the annular segment R) and A ($V_2$=H:A) may be either >1, or =1, or <1.

When $V_2$>1, it is typically from 2 to 10, frequently from 4 to 8 and often 6. When $V_2$<1, it is typically from 0.01 to 0.95, frequently from 0.02 to 0.9, often from 0.03 to 0.8, in many cases from 0.05 to 0.7, or from 0.07 to 0.5 or from 0.1 to 0.4. Possible values for $V_2$ are thus also 0.2 and 0.3.

When $V_2$>1, A is usually from ≥0.5 m to 5 m, frequently from 1 m to 4 m, and appropriately from 2 m to 3 m.

When $V_2$<1, A is typically from ≥0.5 m to 8 m, preferably from 2 m to 7 or 6.50 m and often from 2.5 m to 6 or 5 m.

When $V_2$=1, typical external diameters A are from 0.5 to 8 m, or from 2 to 7 or 6.50 m, or from 2.5 m to 6 or 5 m.

When $V_2$>1, the annular interior (the ring interior) of the annular segment R of the shell E is especially suitable for the configuration of an inventive tray reaction chamber which is flowed through radially and is particularly suitable for the process according to the invention. To this end, the annular interior $I_R$ appropriately comprises fixed catalyst beds poured between the annular gaps of concentric grids, the annular gap advantageously being arranged in sections one on top of another such that a reaction gas flowing through it, after radial passage in one section, is conducted into the next section above it or below it. The number of aforementioned catalyst beds may be from 1 to 20, appropriately from 2 to 8 and preferably from 3 to 6. In other words, preference is given in accordance with the invention to shells E with a ring interior $I_R$ which have annular gaps which are arranged one on top of another in sections and consist of grids concentric in each case and whose $V_2$>1.

When $V_2$<1, the annular interior (the ring interior) of the annular segment R of the shells E is especially suitable for the configuration of an inventive tray reaction chamber which is flowed through axially and is particularly suitable for the process according to the invention. To this end, the annular interior $I_R$ appropriately comprises catalyst beds poured onto grids arranged in axial succession (i.e. along the ring axis or cylinder axis), which are flowed through in succession by the reaction gas. The number of aforementioned catalyst beds may be from 1 to 20, appropriately from 2 to 8 and preferably from 3 to 6. In general, they are arranged equidistantly.

In other words, preference is given in accordance with the invention to shells E having a ring interior $I_R$ which comprise grids arranged in axial succession and whose $V_2$<1. The latter is true especially when H is from 2 m to 4 m (preferably from 2.50 to 3.50 m, e.g. 2.70 m) and the internal diameter of the annular segment R (at a wall thickness of from 1 to 4 cm) is from 5.90 m to 6.50 m. Appropriately, the number of catalyst bed trays arranged in axial succession in the aforementioned case is three. The bed height of a catalyst bed (for example of the catalyst according to Ex. 4 of DE-A 102 19 879) will appropriately be from 10 to 60 cm (e.g. 30 cm).

Appropriately from an application point of view, the two parallel circular planes delimiting the annular segment R are concluded by a hood in each case (supplemented to make shell E). In principle, the hoods may have the form of a flat base (lid) or else be curved. Preference is given in accordance with the invention to hoods curved on both sides of the annular segment R. It is possible for the curvature to have torispherical shape according to DIN 28013 or semiellipsoidal shape according to DIN 28011. The curve of the lower hood will normally point away from the interior $I_R$ (be curved outward, convex). The curvature of the upper hood may be either concave or convex relative to the interior $I_R$. In a simple manner from an application point of view, both hoods are curved convex relative to the interior $I_R$. In this case, the at least one first orifice O1 is appropriately in the center of the upper hood and the at least one second orifice O2 is appropriately in the center of the lower hood (in general, the composite material to be used in accordance with the invention to manufacture the hoods has steel A in a greater wall thickness than the corresponding inventive composite material used to manufacture the annular segment R (with identical selection of the steels A, B), in order to satisfy the requirement for increased pressure rating). In principle, different inventive composite materials comprising steels A, B may be used for the reactor hoods than for the annular segment R. In general, however, the same inventive composite material will be used for the reactor hoods and the annular segment (apart from material thicknesses which may be different if appropriate). The orifices O1 and O2 are preferably circular. Appropriately from an application point of view, their cross sections are selected such that their ratio corresponds to the ratio of the contemplated volume streams flowing in and out through them. At a height H of from 2 m to 4 m (preferably from 2.50 to 3.50 m, e.g. 2.70 m) and an internal diameter of the annular segment of from 5.90 to 6.50 m, the diameter of the at least one first orifice O1 may, for example, typically be 1200 mm and the diameter of the at least one second orifice, O2, for example, typically 1400 mm. Advantageously from an application point of view, the wall thickness of the steel B in the composite material to be used in accordance with the invention for the lower hood is thicker than that for the annular segment R. In this case, the part of the hood wall protruding beyond D may bear the support grids (and catalyst beds) arranged, for example, in axial succession (stacked one on top of another) in the annular segment R.

However, the individual annular grids may also be composed of (assembled from) uniform (separate) circle sectors (grid sectors) (like the cross section of a slice of orange). From an application point of view, preference is given to twelfth, or eighth, or sixth, or quarter, or third circle sectors. The grid circle sectors may in turn rest on open framework circle sectors. The lowermost framework circle sectors may, adjusted to the curvature of the lower hood, be continued and placed into the convex curvature of the lower hood as the element bearing the framework circle sectors. The framework circle sectors of grid sectors disposed above them may then in each case be placed onto those of the catalyst tray disposed immediately below them.

In principle, shells E may be manufactured seamlessly from the annular segment R and the two hoods concluding it. However, the segment R and the hoods are generally manufactured separately and subsequently have to be bonded to one another in a very substantially gas-tight manner (gas leakage <$10^{-4}$ mbar·l/s). In the case of the lower hood, this bonding with the annular segment R is preferably effected by welding it on. In the case of the upper hood, however, the bonding with the annular segment R is advantageously undertaken by flanging it on (the removability of the upper hood eases the filling with and the withdrawal of catalyst, for example in the case of a partial catalyst change or in the case of a full catalyst change). Particular preference is given to a flange bond with weld lip sealing (preferably in accordance with the invention, the latter will be manufactured preferably from metal sheets or semi-finished stainless steel products or nickel-base alloys, in which case the sheet thickness may be, for example, 2 mm).

Advantageously in accordance with the invention, elements (internals) present in the ring interior are manufactured from a steel B. When they are weight-bearing elements (for example the support grids), they are, preferably in accordance with the invention, manufactured from a steel B of EN materials number 1.4835 or from a steel B of DIN materials number 1.4893. In a less preferred embodiment, steel of DIN materials number 1.4541 is also useful for this purpose.

Preferably in accordance with the invention, the shaped catalyst bodies will not be placed directly onto the grids. This is because the shaped catalyst bodies typically have a smaller dimension than the mesh width of the grid. Appropriately, therefore, a layer (height: from 1 to 10 cm, preferably from 5 to 10 cm) of steatite spheres of diameter from 3 to 10 cm, frequently from 4 or 5 to 8 cm, is placed first onto a grid (preference is given to using steatite C220 from CeramTec). In principle, also useful are shaped bodies other than spheres (for example cylinders or rings) which have a longest dimension (longest direct line connecting two points on their surface) corresponding to the aforementioned diameters. Useful alternative inert materials to steatite include in particular aluminum oxides, silicon dioxide, thorium dioxide, zirconium dioxide, silicon carbide or silicates such as magnesium silicate and aluminum silicate. Only to this inert layer is the catalyst bed then applied. The reaction gas flows through the reaction chamber in a corresponding manner from the top downward. At the top, the catalyst bed is covered once again by an appropriate inert bed.

A pipeline feeding the at least one starting gas stream is normally likewise bonded in a gas-tight manner to the at least one first orifice O1 by flanging it on, as is the pipeline removing the at least one product gas stream to the at least one second orifice O2. Alternatively, the flange attachment can also be replaced by welding attachment.

For proper and safe operation, the aforementioned (pipe) lines are preferably equipped with devices for compensating longitudinal expansion effects, as can occur, for example, owing to temperature changes, and it is advantageous to use compensators which feature a lateral mode of action.

These compensators which generally have a multilayer design may be manufactured from the same material as the pipeline itself. However, particularly advantageous embodiments are those with (generally: gas-permeable rigid inner tube and gas-impermeable elastic outer sleeve (gas-impermeable elastic outer tube)) an inner tube part, preferably manufactured from a material to be used in accordance with the invention, which is in contact with the gas to be conducted and appropriately has a gas-permeable expansion joint and an external, gas-impermeable, elastic, corrugated part which is manufactured at least partly from an especially mechanically and thermally stressable material, for example material 1.4876 (designation according to VdTÜV-Wb 434) or 1.4958/1.4959 (designation according to DIN 17459) or INCOLOY® 800H or 800 HT, or nickel-base material 2.4816 (alternative designation Alloy 600) or 2.4851 (alternative designation Alloy 601).

In principle, the shell E, just like the feeding and removing pipelines, can also be manufactured from nickel-base material 2.4642 (alternative designation Alloy 690 or Inconel H 690). However, this material among the materials recommended in this document is the most expensive by far.

In order to minimize the residence time of a gas fed in the interior I of a shell E in a manner advantageous in accordance with the invention, it is appropriate to reduce the inner hood volume by means of displacer bodies mounted within the hood.

Alternatively to the aforementioned approach to a solution, it is advisable to use a concave (into the interior of the annular segment R) curved hood. In this case, the at least one orifice O1 for feeding the at least one gas stream into the interior will advantageously not be mounted in the center of the upper hood. Instead, it is appropriate in this case, appropriately distributed uniformly around the circumference of the uppermost section of the annular segment R, to mount windows with passage to the annular interior $I_R$ as such orifices. From the outside, a ring channel which is attached to the window bar in a gas-tight manner (similarly to the ring channel for feeding salt melt in a salt bath-cooled tube bundle reactor; cf. number 22 in DE-A 198 06 810, FIG. 1) will appropriately be mounted around the window bar. The starting gas stream will then be fed to the ring channel which distributes this gas stream uniformly over all windows and feeds it to the interior $I_R$ through the windows. In the interior $I_R$, impingement plates may be mounted at controlled distance from the windows and additionally uniformize the distribution of the starting gas stream fed to the interior $I_R$ over the cross section of the interior $I_R$.

For the purpose of adiabatic performance of a heterogeneously catalyzed dehydrogenation of at least one hydrocarbon to be dehydrogenated in the interior I (especially in the interior $I_R$) of the shell E, thermal insulation material (=materials which reduce the heat transfer number for the heat transfer from the shell to the environment) will be mounted on the side of the shell E (including hoods and feed and removal lines) facing away from the interior I (for example glass wool, rockwool and/or ceramic wool). If required, the aforementioned insulation materials may additionally be applied to the side of the shell E facing toward the interior. In this case, they may themselves have a separating envelope, for example of inventive steel sheet. Overall, the thermal insulation is preferably such that, based on single pass of the reaction gas through to the interior I, ≤10%, preferably ≤5% and more preferably ≤2% of the heat content averaged over the interior I flows out to the external environment of the shell E during the performance of a process according to the invention in the interior I. For the case of an adiabatic conventional oxidative heterogeneously catalyzed dehydrogenation of at least one hydrocarbon to be dehydrogenated (e.g. propane to propylene), lines will be conducted through the shell E into the interior I, through which, for example, gas comprising molecular oxygen (e.g. air) which serves for exothermic catalytic combustion of molecular hydrogen and, if appropriate, hydrocarbon may be injected between the catalyst trays.

Advantageously in accordance with the invention, these lines are likewise manufactured from a steel B. For this purpose, preference is given to using a steel B of EN materials number 1.4835 or a steel B of DIN materials number 1.4893. Alternatively, these lines can also be manufactured from nickel-base alloy 2.4642 (alternative designation Alloy 690 or Inconel H 690).

As an alternative embodiment, useful shells E for the process according to the invention are also those which describe a hollow sphere. In these cases, the shell E has a hollow spherical zone segment K, which can be imagined as a hollow sphere intersected by two parallel planes. Between the two planes, the hollow spherical zone segment K is then formed and, above and below the two planes, a hollow spherical cap which can assume the function of the hoods outwardly concluding the segment K is cut off in each case. The interior $I_K$ of the segment K is in turn formed by the particularly relevant part of the interior I (corresponding to $I_R$). Otherwise, in the case of a spherical shell E too, everything stated for the cylindrical shell E with regard to the accommodation of catalyst trays and feed and removal orifices O1 and O2 applies analogously. The same applies to the statements on thermal insulation. Around the shell E itself, a support ring will generally advantageously be mounted, which, appropriately placed on four supports, holds the shell E.

When the interior I formed by the shell E comprises internals such as (support) grids, etc., they may also be manufactured for the process according to the invention, for example, from fired clays (aluminum silicates) or steatite (for example C 220 from CeramTec), or other high-temperature ceramic materials such as aluminum oxides, silicon dioxide, thorium dioxide, zirconium dioxide, silicon carbide or other silicates such as magnesium silicate.

Otherwise, the shell E, including the interior I formed by it and its internals, may be configured as in the documents DE 10 2006 017 623.5 and 10 2006 015 235.2. The height of the catalyst bed on the individual tray may, for example, be 40 cm.

When a shell E is manufactured by welding composite material to be used in accordance with the invention, such welding is preferably effected in accordance with the invention with identical materials, i.e. base material and additional welding material are largely identical. In principle, it is also possible for this purpose to use lower-melting steel whose elemental composition approximates very closely to steel to be used in accordance with the invention. In general, in the case of the inventive composite material, welding will commence with the welding of the steel A (the pressure-bearing part). Subsequently, steel B will be welded.

When particular care is taken, it is finally additionally possible to weld a covering strip of steel B onto the weld seam obtained beforehand on the side in contact with the reaction chamber. In principle, the welding can be undertaken as described in DIN EN 1011-5, 2003-10 edition (especially part 5) or as described in Böhler Thyssen Schweisstechnik Deutschland GmbH-09-2005 (especially page 464 ff.). The welding is preferably effected under inert gas atmosphere (more preferably under argon and/or He).

Suitable fusion welding processes are light arc welding with rod electrodes and also protective gas welding (in particular by the WIG method). The protective gas used is preferably an argon-, helium- and/or nitrogen-containing protective gas. The welding electrodes used may be the welding rods Thermanit D (W 22 12H) or Thermanit C (W 25 20 Mn) or Sandvik 22 12 HT.

Finally, it should be noted once again that the steels A impart to the inventive composite material, on the outside, the low long-term embrittlement, and the steels B, on the inside, minimal carburization and minimal metal dusting, and also minimal undesired catalytic action.

EXAMPLES AND COMPARATIVE EXAMPLES

Experimental Description

1. Configuration of the reaction tubes
The geometry of the reaction tubes is:
length 0.55 mm
external diameter (A) from 21.34 to 22 mm
wall thickness (W) from 2 to 2.77 mm The particular reaction tube is filled over its entire length with inert spheres of steatite C 220 from CeramTec. The sphere diameter is from 1.5 mm to 2.5 mm with essentially uniform distribution.

2. The material used for the reaction tube is 7 different materials.
Material 1 (M1): stainless steel of DIN materials number 1.4841 (A=22 mm, W=2 mm),
Material 2 (M2): stainless steel of DIN materials number 1.4541 (A=22 mm, W=2 mm),
Material 3 (M3): stainless steel of DIN materials number 1.4910 (A=22 mm, W=2 mm),
Material 4 (M4): stainless steel of DIN materials number 1.4893 with the following composition (A=21.34 mm, W=2.77 mm):
  20.87% by weight of Cr,
  10.78% by weight of Ni,
  1.54% by weight of Si,
  0.161% by weight of N,
  0.082% by weight of C,
  0.75% by weight of Mn,
  0.02% by weight of P,
  0.0026% by weight of S,
  0.05% by weight of Ce, and,
  apart from these, Fe and impurities resulting from production, the percentages each being based on the total weight.
Material 5 (M5): stainless steel of DIN materials number 1.4841 (wall thickness: 1 mm), applied directly to stainless steel of DIN materials number 1.4910 (wall thickness: 1 mm) (A=22 mm).
Material 6 (M6): nickel-base material 2.4642 (A=22 mm, W=2 mm) with the elemental composition:
  8.70% by weight of Fe,
  27.85% by weight of Cr,
  0.02% by weight of C,
  0.15% by weight of Si,
  0.2% by weight of Mn,
  and, apart from these, Ni and impurities resulting from production, the percentages each being based on the total weight.
Material 7 (M7): stainless steel of DIN materials number 1.4876 (A=22 mm, W=2 mm)

3. The different reaction tubes are each charged with the following starting gas stream, as is typical in its composition for an inventive heterogeneously catalyzed dehydrogenation of propane to propylene:
  34.4% by volume of propane,
  55.6% by volume of nitrogen,
  3.2% by volume of oxygen, and
  6.8% by volume of steam.

4. The reaction tube was in each case mounted in a radiative oven (electrically heated ceramic body with hollow cylindrical guide for accommodating the reaction tube with a gap width of from 0.13 to 0.15 cm to the reaction tube outer wall).

5. The particular reaction tube is flowed through as described (P (reactor outlet pressure)=1 atm) by the starting gas stream (this has an inlet temperature of 200° C. in each case). At the same time, the temperature $T^A$ of the outer wall of the reaction tube is increased such that the maximum temperature $T^M$ in the reaction tube increases from 400° C. to 700° C. in an essentially linear manner with a gradient of 10° C./h (this simulates the compensation of a catalyst bed being deactivated in continuous operation by increasing the reaction temperature).

Subsequently, the regeneration of a dehydrogenation catalyst bed is simulated. To this end, the reaction tube is flowed through first with 420 ml (STP)/min of N$_2$ of inlet temperature 200° C. while keeping the temperature T$^M$ at 700° C.

While retaining the temperature T$^M$=700° C., the following gas flow program is passed through:
over 60 min, lean air (mixture of air (85.4 ml (STP)/min) and N$_2$ ((341.6 ml (STP)/min));
then—over 60 min, 417 ml (STP)/min of air;
then—over 15 min, 417 ml (STP)/min of N$_2$;
then—over 60 min, 168 ml (STP)/min of H$_2$.

The particular reaction tube, flowed through by the particular feed, was then brought from T$^M$=700° C. to T$^M$=400° C. in an essentially linear manner with a T$^M$ gradient of 10° C./h. From attainment of the temperature T$^M$=400° C., the temperature T$^A$ of the outer wall of the reaction tube is in turn increased such that the maximum temperature T$^M$ in the reaction tube increases from 400° C. to 700° C. in an essentially linear manner with a gradient of 10° C./h. Subsequently, as described above, the regeneration of a dehydrogenation catalyst bed is again simulated, etc.

After a total operating time of 1000 h, the particular reaction tube is examined for carburization, metal dusting, long-term embrittlement (comparison of the notched impact resistance KZ before the start of the particular experiment (KZ$_V$) and at the end (KZ$_E$) of performance of the experiment for 1000 hours) (for this purpose, the sample is at room temperature in each case).

The following table shows the resulting results.

|    | Carburization | Metal dusting | Long-term embrittlement | KZ$_V$ [J] | KZ$_E$ [J] |
|----|---------------|---------------|-------------------------|------------|------------|
| M1 | −             | −             | ++                      | >40        | <5         |
| M2 | ++            | +             | −                       | >>40       | >>40       |
| M3 | ++            | +             | −                       | >>40       | >>40       |
| M4 | 0             | −             | +                       | >40        | <10        |
| M5 | −             | −             | −                       | >>40       | >>40       |
| M6 | −             | −             | −                       | >>40       | >>40       |
| M7 | ++            | +             | −                       | >>40       | >>40       |

In the table, the following meanings apply:
−: no occurrence
0: moderate occurrence
+: high occurrence
++: very high occurrence For materials M2, M3, M5, M6 and M7, the values for KZ$_V$ and KZ$_E$ are essentially indistinguishable within the precision of measurement.

In addition, at the start of the particular reaction tube, the amount of propane converted as it passes through the reaction tube is determined (in each case at the temperatures T$^A$=500° C., 600° C., 650° C. and 700° C.

The lowest conversion values are determined in the cases of M1, M5 and M6. The conversions also increase with TA.

U.S. Provisional Patent Application No. 60/816,592, filed on Jun. 27, 2006, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

The invention claimed is:

1. A shell E which encloses an interior I and has at least one first orifice O1 for feeding at least one gas stream S into the interior I, and at least one second orifice O2 for withdrawing a gas stream S from the interior I, wherein the shell E is manufactured from a composite material which, on an interior side B, consists of a steel B of the following elemental composition:
from 18 to 30% by weight of Cr,
from 9 to 37% by weight of Ni,
from 1 to 4% by weight of Si,
from ≥0 to 4% by weight of Al,
from ≥0 to 0.3% by weight of N,
from ≥0 to 0.15% by weight of C,
from ≥0 to 4% by weight of Mn,
from ≥0 to 0.05% by weight of P,
from ≥0 to 0.05% by weight of S, and
from ≥0 to 0.1% by weight of one or more rare earth metals, and
apart from these, Fe and impurities resulting from production, the percentages each being based on the total weight,
with the proviso that the steel B, on an exterior side A is plated either directly or via an intermediate layer of at least one metal selected from the group consisting of copper, nickel, and copper and nickel, onto a steel A of the elemental composition
from 15 to 20% by weight of Cr,
from 6 to 18% by weight of Ni,
from ≥0 to 0.8% by weight of Si,
from ≥0 to 0.8% by weight of Al,
from ≥0 to 0.3% by weight of N,
from ≥0 to 0.15% by weight of C,
from ≥0 to 4% by weight of Mo,
from ≥0 to 2% by weight of Mn,
from ≥0 to 0.8% by weight of Ti,
from ≥0 to 1.2% by weight of Nb,
from ≥0 to 0.9% by weight of V,
from ≥0 to 0.1% by weight of B,
from ≥0 to 0.05% by weight of P,
from ≥0 to 0.05% by weight of S, and
apart from these, Fe and impurities resulting from production, the percentages each being based on the total weight,
or of the elemental composition
from 19 to 23% by weight of Cr,
from 30 to 35% by weight of Ni,
from ≥0 to 1% by weight of Co,
from ≥0 to 1% by weight of Si,
from 0.15 to 0.7% by weight of Al,
from ≥0 to 0.12% by weight of C,
from ≥0 to 2.0% by weight of Mn,
from ≥0 to 0.75% by weight of Cu,
from ≥0.15 to 0.7% by weight of Ti,
from ≥0 to 0.05% by weight of P,
from ≥0 to 0.05% by weight of S, and
apart from these, Fe and impurities resulting from production, the percentages each being based on the total weight.

2. The shell E according to claim 1, wherein the interior I comprises at least one dehydrogenation catalyst.

3. The shell E according to claim 1, wherein the interior I comprises at least one support grid.

4. The shell E according to claim 1, wherein the shell E has an annular segment R.

5. The shell E according to claim 4, wherein a ratio of V$_1$=D:A, wherein D is half of the difference between an external diameter A and an internal diameter of the annular segment R, is from 1:10 to 1:1000.

6. The shell E according to claim 5 where V$_1$ is from 1:40 to 1:500.

7. The shell E according to claim 4, wherein a ratio $V_2$=H:A, wherein A is a separation H of two parallel circular planes delimiting the annular segment R and an external diameter A of the annular segment, is >1.

8. The shell E according to claim 4, wherein a ratio $V_2$=H:A, wherein A is a separation H of two parallel circular planes delimiting the annular segment R and an external diameter A of the annular segment, is ≤1.

9. The shell E according to claim 1 which has a hollow spherical zone segment K in the interior I.

10. The shell E according to claim 1 which has a thermal insulation material on an exterior side facing away from the interior I.

11. The shell E according to claim 1 where the steel B has been subject to at least one treatment selected from the group consisting of alonized, alitized and aluminized, on an interior side B in contact with the interior I.

12. The shell E according to claim 1, wherein the steel A and the steel B of the composite material are austenitic steels.

13. The shell E according to claim 1 which has a thermal insulation material mounted on an interior side B in contact with the interior I.

14. The shell E according to claim 1, wherein the steel B comprises from 0.03 to 0.15% by weight of C and the steel A comprises from 0.03 to 0.15% by weight of C.

15. The shell E according to claim 1, wherein the composite material is manufactured by explosive plating.

16. A reactor comprising the shell E of claim 1 and a catalyst bed in the interior I.

17. The reactor of claim 16 wherein the catalyst bed is a fixed catalyst bed.

18. The shell according to claim 5, wherein $V_1$ is from 1:50 to 1:400.

19. The shell E according to claim 1, wherein the steel B comprises from 11 to 37% by weight of Ni.

20. The shell E according to claim 1, wherein the steel B comprises from 12 to 37% by weight of Ni.

* * * * *